(12) United States Patent
Bedingfield

(10) Patent No.: US 7,998,115 B2
(45) Date of Patent: Aug. 16, 2011

(54) DIALYSIS SYSTEM HAVING OPTICAL FLOWRATE DETECTION

(75) Inventor: John Bedingfield, Largo, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1088 days.

(21) Appl. No.: 11/675,469

(22) Filed: Feb. 15, 2007

(65) Prior Publication Data

US 2008/0200865 A1 Aug. 21, 2008

(51) Int. Cl.
*A61M 37/00* (2006.01)
*A61M 1/00* (2006.01)
*F04B 43/12* (2006.01)
*E03B 1/00* (2006.01)

(52) U.S. Cl. ............ 604/131; 417/477.2; 137/2; 604/29
(58) Field of Classification Search .............. 604/29, 604/131, 66; 250/573; 210/636
See application file for complete search history.

(56) References Cited

U.S. PATENT DOCUMENTS

| | | | |
|---|---|---|---|
| 2,295,366 A * | 9/1942 | Stout | 137/2 |
| 2,705,223 A | 3/1955 | Renfrew et al. | |
| 2,971,876 A | 2/1961 | Phair | |
| 3,255,923 A | 6/1966 | Soto | |
| 3,375,300 A | 3/1968 | Ropp | |
| 3,428,828 A | 2/1969 | Korzekwa et al. | |
| 3,494,897 A | 2/1970 | Reding et al. | |
| 3,507,708 A | 4/1970 | Vingnaud | |
| 3,514,359 A | 5/1970 | Frese | |
| 3,561,493 A | 2/1971 | Maillard | |
| 3,645,992 A | 2/1972 | Elston | |
| 3,772,136 A | 11/1973 | Workman | |
| 3,814,799 A | 6/1974 | Wygasch | |
| 3,816,033 A | 6/1974 | Fried et al. | |
| 3,858,581 A | 1/1975 | Kamen | |
| 3,912,843 A | 10/1975 | Brazier | |
| 3,937,758 A | 2/1976 | Castagna | |
| 3,946,731 A * | 3/1976 | Lichtenstein | 604/66 |
| 3,995,084 A | 11/1976 | Berger et al. | |
| 4,041,103 A | 8/1977 | Davison et al. | |
| 4,058,647 A | 11/1977 | Inoue et al. | |
| 4,071,040 A | 1/1978 | Moriarty | |

(Continued)

FOREIGN PATENT DOCUMENTS

DE 133 411 Z * 1/1979

(Continued)

OTHER PUBLICATIONS

U.S. Appl. No. 11/675,470, filed Feb. 15, 2007, Prisco, et al.*

(Continued)

*Primary Examiner* — Theodore J Stigell
*Assistant Examiner* — Bradley G Thomas, Jr.
(74) *Attorney, Agent, or Firm* — K&L Gates LLP

(57) ABSTRACT

A medical fluid machine includes an enclosure; a disposable unit accepted by the enclosure, the disposable unit including a conduit through which a medical fluid can flow, the conduit including a viewing portion; a light source configured and arranged to emit light onto the viewing portion of the conduit; a camera focused on the viewing portion of the conduit; and a processor configured to determine a speed of a particle entrained in the medical fluid based on at least two images of the particle in the viewing area taken by the camera.

20 Claims, 11 Drawing Sheets

U.S. PATENT DOCUMENTS

| | | |
|---|---|---|
| 4,087,587 A | 5/1978 | Shida et al. |
| 4,087,588 A | 5/1978 | Shida et al. |
| 4,095,012 A | 6/1978 | Schirmer |
| 4,110,303 A | 8/1978 | Gergen et al. |
| 4,122,947 A | 10/1978 | Falla |
| 4,137,915 A | 2/1979 | Kamen |
| 4,140,118 A | 2/1979 | Jassawalla |
| 4,142,524 A | 3/1979 | Jassawalla et al. |
| 4,147,827 A | 4/1979 | Breidt, Jr. et al. |
| 4,181,245 A | 1/1980 | Garrett et al. |
| 4,187,057 A | 2/1980 | Xanthopoulos |
| 4,211,519 A | 7/1980 | Hogan |
| 4,233,367 A | 11/1980 | Ticknor et al. |
| 4,236,880 A | 12/1980 | Archibald |
| 4,243,619 A | 1/1981 | Fraser et al. |
| 4,265,601 A | 5/1981 | Mandroian |
| 4,276,175 A * | 6/1981 | Bower .......................... 210/636 |
| 4,286,597 A | 9/1981 | Gajewski et al. |
| 4,298,714 A | 11/1981 | Levin et al. |
| 4,303,376 A | 12/1981 | Siekmann |
| 4,322,465 A | 3/1982 | Webster |
| 4,322,480 A | 3/1982 | Tuller et al. |
| D264,134 S | 4/1982 | Xanthopoulos |
| 4,327,726 A | 5/1982 | Kwong et al. |
| 4,332,655 A | 6/1982 | Berejka |
| 4,333,088 A | 6/1982 | Diggins |
| 4,336,352 A | 6/1982 | Sakurai et al. |
| 4,381,005 A | 4/1983 | Bujan |
| 4,382,753 A | 5/1983 | Archibald |
| 4,387,184 A | 6/1983 | Coquard et al. |
| 4,391,600 A | 7/1983 | Archibald |
| 4,405,667 A | 9/1983 | Christensen et al. |
| 4,405,774 A | 9/1983 | Miwa et al. |
| 4,407,877 A | 10/1983 | Rasmussen |
| 4,407,888 A | 10/1983 | Crofts |
| 4,408,774 A | 10/1983 | Raskob |
| 4,410,164 A | 10/1983 | Kamen |
| 4,410,322 A | 10/1983 | Archibald |
| 4,411,649 A | 10/1983 | Kamen |
| 4,417,753 A | 11/1983 | Bacehowski |
| 4,429,076 A | 1/1984 | Saito et al. |
| 4,438,238 A | 3/1984 | Fukushima et al. |
| 4,449,976 A | 5/1984 | Kamen |
| 4,472,116 A | 9/1984 | Wenstrup |
| 4,472,117 A | 9/1984 | Wenstrup |
| 4,473,342 A | 9/1984 | Iles |
| 4,479,760 A | 10/1984 | Bilstad et al. |
| 4,479,761 A | 10/1984 | Bilstad et al. |
| 4,479,762 A | 10/1984 | Bilstad et al. |
| 4,479,989 A | 10/1984 | Mahal |
| 4,521,437 A | 6/1985 | Storms |
| 4,537,561 A | 8/1985 | Xanthopoulos |
| 4,547,136 A | 10/1985 | Rothstein |
| 4,548,348 A | 10/1985 | Clements |
| 4,562,118 A | 12/1985 | Maruhashi et al. |
| 4,568,723 A | 2/1986 | Lu |
| 4,573,994 A | 3/1986 | Fischell et al. |
| 4,574,173 A | 3/1986 | Bennett |
| 4,586,920 A | 5/1986 | Peabody |
| 4,588,648 A | 5/1986 | Krueger |
| 4,599,055 A | 7/1986 | Dykstra |
| 4,599,276 A | 7/1986 | Martini |
| 4,600,401 A | 7/1986 | Kamen |
| 4,620,690 A | 11/1986 | Kamen |
| 4,627,844 A | 12/1986 | Schmitt |
| 4,628,969 A | 12/1986 | Jurgens, Jr. et al. |
| 4,634,426 A | 1/1987 | Kamen |
| 4,636,412 A | 1/1987 | Field |
| 4,640,870 A | 2/1987 | Akazawa et al. |
| 4,642,098 A | 2/1987 | Lundquist |
| 4,643,926 A | 2/1987 | Mueller |
| 4,648,872 A | 3/1987 | Kamen |
| 4,657,490 A | 4/1987 | Abbott |
| 4,668,752 A | 5/1987 | Tominari et al. |
| 4,673,334 A | 6/1987 | Allington et al. |
| 4,681,797 A | 7/1987 | Van Iseghem |
| 4,686,125 A | 8/1987 | Johnston et al. |
| 4,692,361 A | 9/1987 | Johnston et al. |
| 4,696,671 A | 9/1987 | Epstein et al. |
| 4,707,389 A | 11/1987 | Ward |
| 4,724,028 A | 2/1988 | Zabielski et al. |
| 4,726,997 A | 2/1988 | Mueller et al. |
| 4,732,795 A | 3/1988 | Ohya et al. |
| 4,734,327 A | 3/1988 | Vicik |
| 4,735,558 A | 4/1988 | Kienholz et al. |
| 4,735,855 A | 4/1988 | Wofford et al. |
| 4,740,582 A | 4/1988 | Coquard et al. |
| 4,749,109 A | 6/1988 | Kamen |
| 4,753,222 A | 6/1988 | Morishita |
| 4,760,114 A | 7/1988 | Haaf et al. |
| 4,762,864 A | 8/1988 | Goel et al. |
| 4,764,404 A | 8/1988 | Genske et al. |
| 4,767,377 A | 8/1988 | Falla |
| 4,767,651 A | 8/1988 | Starczweski et al. |
| 4,772,497 A | 9/1988 | Maasola |
| 4,778,450 A | 10/1988 | Kamen |
| 4,778,451 A | 10/1988 | Kamen |
| 4,778,697 A | 10/1988 | Genske et al. |
| 4,786,697 A | 11/1988 | Cozewith et al. |
| 4,789,714 A | 12/1988 | Cozewith et al. |
| 4,792,488 A | 12/1988 | Schirmer |
| 4,794,942 A | 1/1989 | Yasuda et al. |
| 4,795,782 A | 1/1989 | Lutz et al. |
| 4,798,580 A | 1/1989 | DeMeo et al. |
| 4,800,129 A | 1/1989 | Deak |
| 4,803,102 A | 2/1989 | Raniere et al. |
| 4,808,161 A | 2/1989 | Kamen |
| 4,816,343 A | 3/1989 | Mueller |
| 4,818,190 A | 4/1989 | Pelmulder et al. |
| 4,824,339 A | 4/1989 | Bainbridge et al. |
| 4,826,482 A | 5/1989 | Kamen |
| 4,834,755 A | 5/1989 | Silvestrini et al. |
| 4,842,948 A | 6/1989 | Gagliani et al. |
| 4,848,722 A | 7/1989 | Webster |
| 4,852,851 A | 8/1989 | Webster |
| 4,855,356 A | 8/1989 | Holub et al. |
| 4,856,259 A | 8/1989 | Woo et al. |
| 4,856,260 A | 8/1989 | Woo et al. |
| 4,861,242 A | 8/1989 | Finsterwald |
| 4,863,996 A | 9/1989 | Nakazima et al. |
| 4,871,799 A | 10/1989 | Kobayashi et al. |
| 4,872,813 A | 10/1989 | Gorton et al. |
| 4,873,287 A | 10/1989 | Holub et al. |
| 4,877,682 A | 10/1989 | Sauers et al. |
| 4,885,119 A | 12/1989 | Mueller et al. |
| 4,886,431 A | 12/1989 | Soderquist et al. |
| 4,904,168 A | 2/1990 | Cavoto et al. |
| 4,910,085 A | 3/1990 | Raniere et al. |
| 4,923,470 A | 5/1990 | Dumican |
| 4,929,479 A | 5/1990 | Shishido et al. |
| 4,931,520 A | 6/1990 | Yamanashi et al. |
| 4,937,299 A | 6/1990 | Ewen et al. |
| 4,941,519 A | 7/1990 | Sestak et al. |
| 4,946,616 A | 8/1990 | Falla et al. |
| 4,950,720 A | 8/1990 | Randall, Jr. et al. |
| 4,957,966 A | 9/1990 | Nishio et al. |
| 4,957,967 A | 9/1990 | Mizuno et al. |
| 4,966,795 A | 10/1990 | Genske et al. |
| 4,976,162 A | 12/1990 | Kamen |
| 4,977,213 A | 12/1990 | Giroud-Abel et al. |
| 4,990,054 A | 2/1991 | Janocko |
| 4,992,511 A | 2/1991 | Yamamoto et al. |
| 4,996,054 A | 2/1991 | Pietsch et al. |
| 4,999,254 A | 3/1991 | Ofstein |
| 5,003,019 A | 3/1991 | Ishimaru et al. |
| 5,006,601 A | 4/1991 | Lutz et al. |
| 5,008,204 A | 4/1991 | Stehling |
| 5,008,356 A | 4/1991 | Ishimaru et al. |
| 5,017,652 A | 5/1991 | Abe et al. |
| 5,019,140 A | 5/1991 | Bowser et al. |
| 5,034,457 A | 7/1991 | Serini et al. |
| 5,034,458 A | 7/1991 | Serini et al. |
| 5,043,088 A | 8/1991 | Falla |
| 5,044,902 A | 9/1991 | Malbec |
| 5,053,457 A | 10/1991 | Lee |
| 5,062,774 A | 11/1991 | Kramer et al. |
| 5,071,686 A | 12/1991 | Genske et al. |

| | | | | | | |
|---|---|---|---|---|---|---|
| 5,071,911 A | 12/1991 | Furuta et al. | | 5,364,371 A * | 11/1994 | Kamen |
| 5,071,912 A | 12/1991 | Furuta et al. | | 5,364,486 A * | 11/1994 | Falla et al. |
| 5,075,376 A | 12/1991 | Furuta et al. | | 5,371,151 A * | 12/1994 | Berge et al. |
| 5,079,295 A | 1/1992 | Furuta et al. | | 5,378,543 A * | 1/1995 | Murata et al. |
| 5,085,649 A | 2/1992 | Flynn | | 5,378,800 A * | 1/1995 | Mok et al. |
| 5,087,677 A | 2/1992 | Brekner et al. | | 5,382,630 A * | 1/1995 | Stehling et al. |
| 5,088,515 A | 2/1992 | Kamen | | 5,382,631 A * | 1/1995 | Stehling et al. |
| 5,093,164 A | 3/1992 | Bauer et al. | | 5,385,540 A * | 1/1995 | Abbott et al. |
| 5,093,194 A | 3/1992 | Touhsaent et al. | | 5,387,645 A * | 2/1995 | Montag et al. |
| 5,094,820 A | 3/1992 | Maxwell et al. | | 5,397,222 A * | 3/1995 | Moss et al. |
| 5,094,921 A | 3/1992 | Itamura et al. | | 5,401,342 A * | 3/1995 | Vincent et al. |
| 5,098,262 A | 3/1992 | Wecker et al. | | 5,409,355 A * | 4/1995 | Brooke |
| 5,106,366 A | 4/1992 | Steppe | | 5,421,823 A * | 6/1995 | Kamen et al. |
| 5,108,844 A | 4/1992 | Blumberg et al. | | 5,422,409 A * | 6/1995 | Brekner et al. |
| 5,110,642 A | 5/1992 | Genske | | 5,427,509 A * | 6/1995 | Chapman et al. |
| 5,116,906 A | 5/1992 | Mizuno et al. | | 5,429,485 A * | 7/1995 | Dodge |
| 5,125,891 A | 6/1992 | Hossain et al. | | 5,431,626 A * | 7/1995 | Bryant et al. |
| 5,129,894 A | 7/1992 | Sommermeyer et al. | | 5,433,588 A * | 7/1995 | Monk et al. |
| 5,132,363 A | 7/1992 | Furuta et al. | | 5,438,510 A * | 8/1995 | Bryant et al. |
| 5,133,650 A | 7/1992 | Sunderland et al. | | 5,439,587 A | 8/1995 | Stankowski et al. |
| 5,135,485 A | 8/1992 | Cohen et al. | | 5,442,919 A | 8/1995 | Wilhelm |
| 5,135,785 A | 8/1992 | Millon | | 5,445,506 A | 8/1995 | Afflerbaugh et al. |
| 5,145,731 A | 9/1992 | Lund et al. | | 5,446,270 A | 8/1995 | Chamberlain et al. |
| 5,154,979 A | 10/1992 | Kerschbaumer et al. | | 5,457,249 A | 10/1995 | Sagane et al. |
| 5,159,004 A | 10/1992 | Furuta et al. | | 5,460,490 A | 10/1995 | Carr et al. |
| 5,164,267 A | 11/1992 | D'Heur et al. | | 5,460,493 A | 10/1995 | Deniega et al. |
| 5,176,634 A | 1/1993 | Smith et al. | | 5,462,416 A | 10/1995 | Dennehy et al. |
| 5,176,956 A | 1/1993 | Jevne et al. | | 5,464,388 A | 11/1995 | Merte et al. |
| 5,178,182 A | 1/1993 | Kamen | | 5,474,683 A | 12/1995 | Bryant et al. |
| 5,183,706 A | 2/1993 | Bekele | | 5,475,060 A | 12/1995 | Brekner et al. |
| 5,185,084 A | 2/1993 | Lapidus et al. | | 5,480,294 A | 1/1996 | Di Perna et al. |
| 5,185,189 A | 2/1993 | Stenger et al. | | 5,482,440 A | 1/1996 | Dennehey et al. |
| 5,189,091 A | 2/1993 | Laughner | | 5,482,770 A | 1/1996 | Bekele |
| 5,193,913 A | 3/1993 | Rosenbaum | | 5,487,649 A | 1/1996 | Dorsey, III et al. |
| 5,193,990 A | 3/1993 | Kamen et al. | | 5,498,677 A | 3/1996 | Weller |
| 5,194,316 A | 3/1993 | Horner et al. | | 5,508,051 A | 4/1996 | Falla et al. |
| 5,195,960 A | 3/1993 | Hossain et al. | | 5,518,378 A | 5/1996 | Neftel et al. |
| 5,195,986 A | 3/1993 | Kamen | | 5,522,769 A | 6/1996 | DeGuiseppi |
| 5,196,254 A | 3/1993 | Alliyama | | 5,525,659 A | 6/1996 | Falla et al. |
| 5,203,943 A | 4/1993 | Nornberg et al. | | 5,526,844 A | 6/1996 | Kamen |
| 5,206,290 A | 4/1993 | Mizuno et al. | | 5,529,708 A | 6/1996 | Palmgren et al. |
| 5,207,983 A | 5/1993 | Liebert et al. | | 5,530,065 A | 6/1996 | Farley et al. |
| 5,211,201 A | 5/1993 | Kamen et al. | | 5,533,589 A | 7/1996 | Critzer |
| 5,212,238 A | 5/1993 | Schelbelhoffer et al. | | 5,534,606 A | 7/1996 | Bennett et al. |
| 5,213,483 A | 5/1993 | Flaherty et al. | | 5,540,808 A | 7/1996 | Vincent et al. |
| 5,215,312 A | 6/1993 | Knappe et al. | | 5,542,919 A | 8/1996 | Simon et al. |
| 5,218,048 A | 6/1993 | Abe et al. | | 5,552,504 A | 9/1996 | Bennett et al. |
| 5,218,049 A | 6/1993 | Yamamoto et al. | | 5,554,013 A | 9/1996 | Owens et al. |
| 5,222,946 A | 6/1993 | Kamen | | 5,569,026 A | 10/1996 | Novak |
| 5,230,934 A | 7/1993 | Sakano et al. | | 5,570,716 A | 11/1996 | Kamen et al. |
| 5,230,935 A | 7/1993 | Delimoy et al. | | 5,575,310 A | 11/1996 | Kamen et al. |
| 5,238,997 A | 8/1993 | Bauer et al. | | 5,575,632 A | 11/1996 | Morris et al. |
| 5,241,985 A | 9/1993 | Faust et al. | | 5,578,012 A | 11/1996 | Kamen et al. |
| 5,244,971 A | 9/1993 | Jean-Marc | | 5,580,914 A | 12/1996 | Falla et al. |
| 5,245,151 A | 9/1993 | Chamberlain et al. | | 5,583,192 A | 12/1996 | Bennett et al. |
| 5,252,044 A | 10/1993 | Raines et al. | | 5,586,868 A | 12/1996 | Lawless et al. |
| 5,254,824 A | 10/1993 | Chamberlain et al. | | 5,588,815 A | 12/1996 | Zaleski, II |
| 5,257,917 A | 11/1993 | Minarik et al. | | 5,588,816 A | 12/1996 | Abbott et al. |
| 5,258,230 A | 11/1993 | La Fleur et al. | | 5,601,420 A | 2/1997 | Warner et al. |
| 5,272,235 A | 12/1993 | Wakatsuru et al. | | 5,609,572 A | 3/1997 | Lang |
| 5,278,231 A | 1/1994 | Chundury | | 5,610,253 A | 3/1997 | Hatke et al. |
| 5,278,377 A | 1/1994 | Tsai | | 5,620,312 A | 4/1997 | Hyman et al. |
| 5,288,531 A | 2/1994 | Falla et al. | | 5,620,425 A | 4/1997 | Hefferman et al. |
| 5,288,560 A | 2/1994 | Sudo et al. | | 5,628,908 A | 5/1997 | Kamen et al. |
| 5,288,799 A | 2/1994 | Schmidt et al. | | 5,629,398 A | 5/1997 | Okamoto et al. |
| 5,290,856 A | 3/1994 | Okamoto | | 5,634,896 A | 6/1997 | Bryant et al. |
| 5,294,763 A | 3/1994 | Chamberlain et al. | | 5,637,100 A | 6/1997 | Sudo |
| 5,302,093 A * | 4/1994 | Owens et al. | | 5,637,400 A | 6/1997 | Brekner et al. |
| 5,306,542 A * | 4/1994 | Bayer | | 5,650,471 A | 7/1997 | Abe et al. |
| 5,312,867 A * | 5/1994 | Mitsuno et al. | | 5,655,897 A | 8/1997 | Neftel et al. |
| 5,317,059 A * | 5/1994 | Chundury et al. | | 5,674,944 A | 10/1997 | Falla et al. |
| 5,331,057 A * | 7/1994 | Brekner et al. | | 5,676,530 A | 10/1997 | Nazarifar |
| 5,336,190 A * | 8/1994 | Moss et al. | | 5,686,527 A | 11/1997 | Laurin et al. |
| 5,342,886 A * | 8/1994 | Glotin et al. | | 5,693,728 A | 12/1997 | Okamoto et al. |
| 5,348,794 A * | 9/1994 | Takahashi | | 5,698,645 A | 12/1997 | Weller et al. |
| 5,350,357 A * | 9/1994 | Kamen et al. | | 5,698,654 A | 12/1997 | Nye et al. |
| 5,356,676 A * | 10/1994 | Von Widdern et al. | | 5,707,751 A | 1/1998 | Garza et al. |
| 5,359,001 A * | 10/1994 | Epple et al. | | 5,711,654 A | 1/1998 | Afflerbaugh |
| 5,360,648 A * | 11/1994 | Falla et al. | | 5,718,569 A | 2/1998 | Holst |

| | | | |
|---|---|---|---|
| 5,721,025 A | 2/1998 | Falla et al. | |
| 5,723,189 A | 3/1998 | Sudo | |
| 5,733,991 A | 3/1998 | Rohrman et al. | |
| 5,741,125 A | 4/1998 | Neftel et al. | |
| 5,741,213 A | 4/1998 | Kouchi et al. | |
| 5,744,664 A | 4/1998 | Brekner et al. | |
| 5,752,813 A | 5/1998 | Tyner et al. | |
| 5,756,623 A | 5/1998 | Krueder et al. | |
| 5,782,575 A | 7/1998 | Vincent et al. | |
| 5,788,670 A | 8/1998 | Reinhard et al. | |
| 5,788,671 A | 8/1998 | Johnson | |
| 5,792,824 A | 8/1998 | Natori | |
| 5,795,945 A | 8/1998 | Natori | |
| 5,816,779 A | 10/1998 | Lawless et al. | |
| 5,849,843 A | 12/1998 | Laurin et al. | |
| 5,854,347 A | 12/1998 | Laurin et al. | |
| 5,854,349 A | 12/1998 | Abe et al. | |
| 5,863,986 A | 1/1999 | Herrmann-Schonherr et al. | |
| 5,871,566 A | 2/1999 | Rutz | |
| 5,872,201 A | 2/1999 | Cheung et al. | |
| 5,879,768 A | 3/1999 | Falla et al. | |
| 5,899,674 A | 5/1999 | Jung et al. | |
| 5,906,598 A | 5/1999 | Giesler et al. | |
| 5,927,956 A | 7/1999 | Lim et al. | |
| 5,928,196 A | 7/1999 | Johnson et al. | |
| 5,931,808 A | 8/1999 | Pike | |
| 5,942,579 A | 8/1999 | Falla et al. | |
| 5,980,495 A | 11/1999 | Heinz et al. | |
| 5,983,136 A | 11/1999 | Kamen | |
| 5,984,762 A | 11/1999 | Tedeschi et al. | |
| 5,989,423 A | 11/1999 | Kamen et al. | |
| 5,990,254 A | 11/1999 | Weller et al. | |
| 5,993,949 A | 11/1999 | Rosenbaum et al. | |
| 5,998,019 A * | 12/1999 | Rosenbaum et al. | |
| 6,001,201 A * | 12/1999 | Vincent et al. | |
| 6,007,520 A * | 12/1999 | Sudo | |
| 6,013,921 A | 1/2000 | Moller et al. | |
| 6,020,444 A * | 2/2000 | Riedel et al. | |
| 6,036,458 A * | 3/2000 | Cole et al. | |
| 6,045,648 A * | 4/2000 | Palmgren et al. | |
| 6,056,522 A * | 5/2000 | Johnson | |
| 6,059,544 A * | 5/2000 | Jung et al. | |
| 6,060,572 A * | 5/2000 | Gillis et al. | |
| 6,065,270 A * | 5/2000 | Reinhard et al. | |
| 6,068,936 A * | 5/2000 | Pfeiffer et al. | |
| 6,070,761 A * | 6/2000 | Bloom et al. | |
| 6,074,183 A * | 6/2000 | Allen et al. | |
| 6,077,246 A * | 6/2000 | Kullas et al. | |
| 6,106,948 A * | 8/2000 | Wang et al. | |
| 6,109,895 A * | 8/2000 | Ray et al. | |
| 6,110,549 A * | 8/2000 | Hamada et al. | |
| 6,110,617 A * | 8/2000 | Feres | |
| 6,114,457 A * | 9/2000 | Markel et al. | |
| 6,117,465 A * | 9/2000 | Falla et al. | |
| 6,121,394 A * | 9/2000 | Sugimoto et al. | |
| 6,129,699 A * | 10/2000 | Haight et al. | |
| 6,136,744 A * | 10/2000 | Gillis et al. | |
| 6,147,025 A * | 11/2000 | Gillis et al. | |
| 6,165,154 A * | 12/2000 | Gray et al. | |
| 6,168,862 B1 * | 1/2001 | Rosenbaum et al. | |
| 6,169,052 B1 * | 1/2001 | Brekner et al. | |
| 6,171,670 B1 * | 1/2001 | Sudo et al. | |
| 6,186,752 B1 * | 2/2001 | Deniega et al. | |
| 6,191,254 B1 * | 2/2001 | Falla et al. | |
| 6,203,296 B1 * | 3/2001 | Ray et al. | |
| 6,210,361 B1 | 4/2001 | Kamen et al. | |
| 6,221,648 B1 | 4/2001 | La Page et al. | |
| 6,225,426 B1 | 5/2001 | Gillis et al. | |
| 6,225,427 B1 | 5/2001 | Burton et al. | |
| 6,231,320 B1 | 5/2001 | Lawless et al. | |
| 6,234,997 B1 | 5/2001 | Kamen et al. | |
| RE37,208 E | 6/2001 | Winter et al. | |
| 6,248,093 B1 | 6/2001 | Moberg | |
| 6,255,396 B1 | 7/2001 | Ding et al. | |
| 6,261,655 B1 | 7/2001 | Rosenbaum et al. | |
| 6,266,664 B1 | 7/2001 | Russell-Falla et al. | |
| 6,280,408 B1 | 8/2001 | Sipin | |
| 6,293,926 B1 | 9/2001 | Sorensen et al. | |
| 6,302,653 B1 | 10/2001 | Bryant et al. | |
| 6,343,614 B1 | 2/2002 | Gray et al. | |
| 6,364,857 B1 | 4/2002 | Gray et al. | |
| 6,372,848 B1 | 4/2002 | Yang et al. | |
| 6,382,923 B1 | 5/2002 | Gray | |
| 6,416,293 B1 | 7/2002 | Bouchard | |
| 6,497,676 B1 | 12/2002 | Childers et al. | |
| 6,503,062 B1 | 1/2003 | Gray et al. | |
| 6,592,542 B2 | 7/2003 | Childers et al. | |
| 6,808,369 B2 | 10/2004 | Gray et al. | |
| 6,814,547 B2 | 11/2004 | Childers et al. | |
| 6,869,538 B2 | 3/2005 | Yu et al. | |
| 2002/0077598 A1 | 6/2002 | Yap et al. | |
| 2003/0195454 A1 | 10/2003 | Wariar et al. | |
| 2003/0204162 A1 | 10/2003 | Childers et al. | |
| 2004/0254513 A1 * | 12/2004 | Shang et al. | |
| 2005/0118038 A1 * | 6/2005 | Grey et al. | |
| 2006/0175561 A1 * | 8/2006 | Estevadeordal et al. | 250/573 |

FOREIGN PATENT DOCUMENTS

| | | |
|---|---|---|
| DE | 251 904 A3 * | 12/1987 |
| DE | 39 37 365 A1 * | 6/1990 |
| EP | 0 156 464 A1 * | 10/1985 |
| EP | 0 291 208 A2 * | 11/1988 |
| EP | 0 306 664 A2 * | 3/1989 |
| EP | 0 216 509 B1 * | 9/1991 |
| EP | 0 497 567 A2 * | 8/1992 |
| EP | 0 524 802 A1 * | 1/1993 |
| EP | 0 283 164 B1 * | 5/1995 |
| EP | 0 492 982 B1 * | 8/1995 |
| EP | 0 430 585 B1 * | 1/1996 |
| EP | 0 156 464 B1 * | 5/1996 |
| EP | 0 582 355 B1 * | 5/1996 |
| EP | 0 709 105 A1 * | 5/1996 |
| EP | 0 203 799 B1 * | 8/1996 |
| EP | 0 384 694 B1 * | 9/1996 |
| EP | 0 497 567 B1 * | 9/1996 |
| EP | 0 291 208 B1 * | 8/1997 |
| EP | 0 790 063 A1 * | 8/1997 |
| EP | 0 680 401 B1 * | 1/1999 |
| EP | 0 709 105 B1 * | 12/2001 |
| EP | 1466637 | 10/2004 |
| GB | 1 541 419 A | 2/1979 |
| JP | 03-095286 | 4/1991 |
| JP | 05-277154 | 10/1993 |
| JP | 11-071554 | 3/1999 |
| WO | 97/08054 | 3/1997 |
| WO | 98/27926 | 7/1998 |
| WO | 98/44043 | 10/1998 |
| WO | WO 9848867 | 11/1998 |
| WO | 99/48990 | 9/1999 |
| WO | WO 9963882 | 12/1999 |

OTHER PUBLICATIONS

The Notification Concerning Transmittal of International Preliminary Report on Patentability for International Application No. PCT/US2008/053804 mailed Aug. 27, 2009.

Written Opinion of the International Searching Authority for International Application No. PCT/US2008/053804 dated Nov. 20, 2008.

European Search Report for Application No. 08 729 725.5-1257 dated Feb. 4, 2011.

* cited by examiner

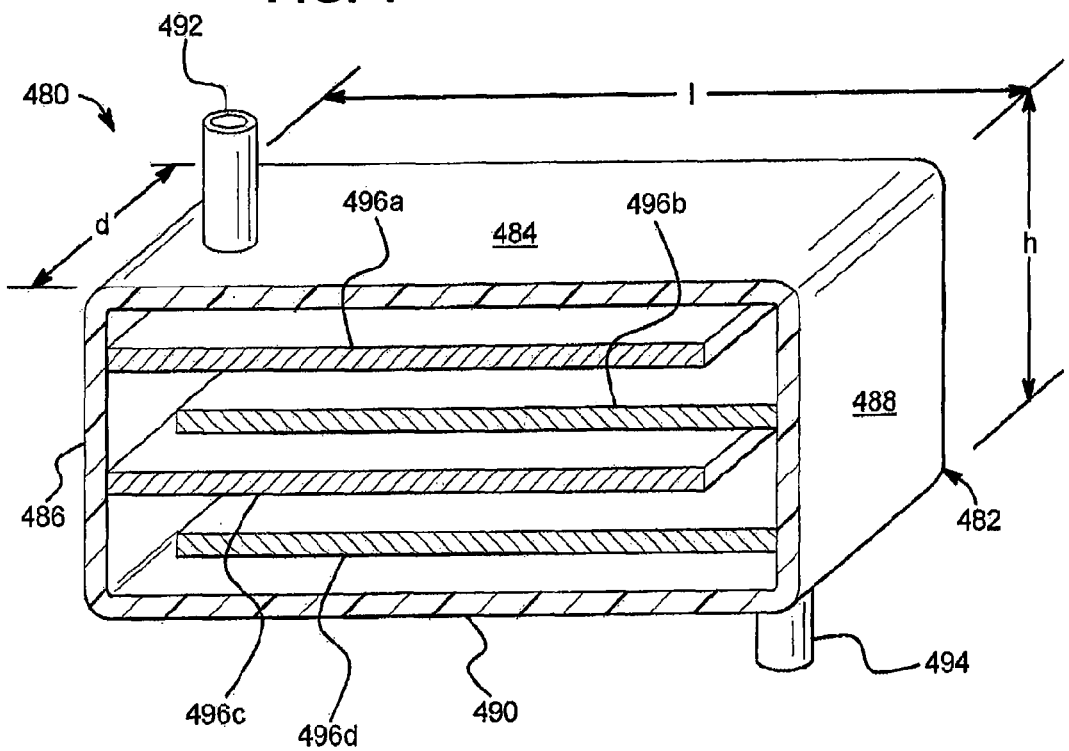
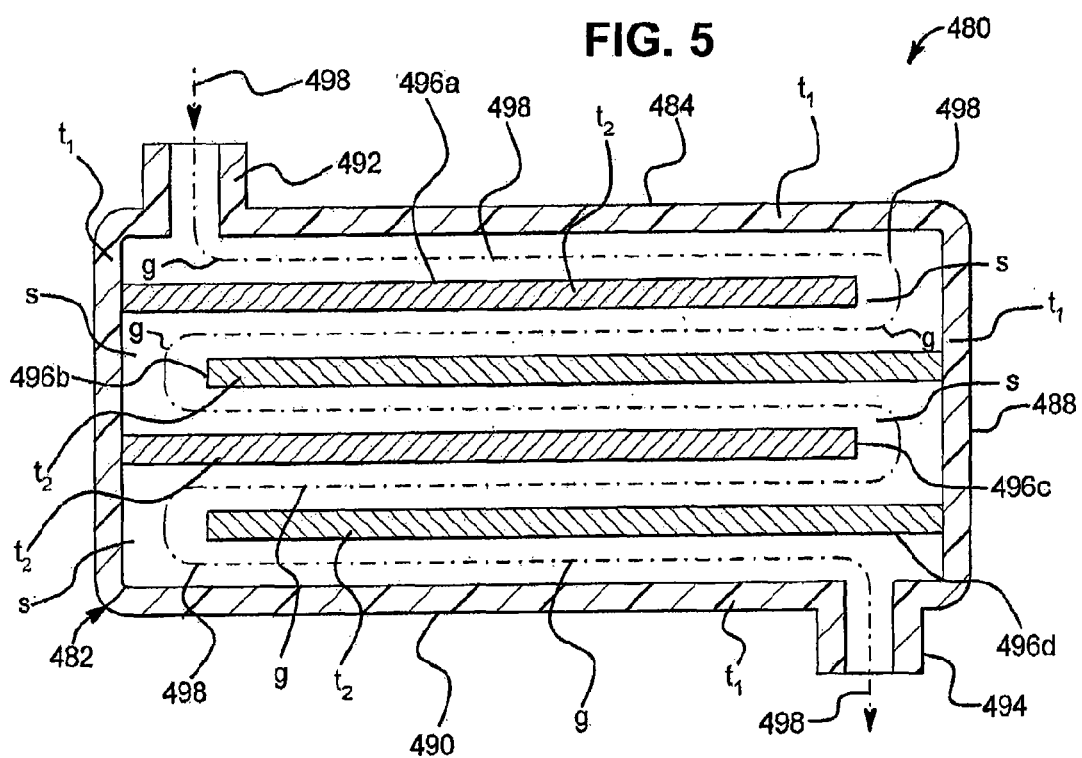

ABSTRACT# DIALYSIS SYSTEM HAVING OPTICAL FLOWRATE DETECTION

BACKGROUND

In general, the present disclosure relates to medical fluid delivery systems that employ a pumping cassette. In particular, the present disclosure provides systems, methods and apparatuses for cassette-based dialysis medical fluid therapies, including but not limited to those using peristaltic pumps and diaphragm pumps.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, or "dialysate," which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Hemodialysis, APD (including tidal flow) and CFPD systems can employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes.

One problem with dialysis systems is to be able to accurately measure dialysate flowrate. Accurate flowrate measurement can be difficult in systems intending to use a sealed disposable cassette. As discussed above, detecting air or gas in dialysis systems is important. It is also useful to be able to detect fibrin in PD systems. In both cases, it would be useful to be able to detect for example the size and/or shape of the gas bubbles or fibrin particles for quantification.

Yet a further concern for dialysis systems is fluid or dialysate temperature heating. The dialysate needs to be heated to roughly body temperature or 37° C. before being delivered to the patient. For dialysate heating, it is desirable to have an apparatus that can be incorporated into, at least partially, and/or operate with a disposable dialysis cassette.

The present disclosure address the above-described needs and concerns.

SUMMARY

A first aspect of the present disclosure includes an improved system for medical fluid flowrate detection. The system may be implemented in a disposable cassette or with tubing operating with a disposable cassette, for example. A portion of a cassette pathway or the tube is flattened, e.g., into a section having a known, rectangular cross-sectional area. The rectangular shape can have a high aspect ratio, that is, is relatively thin in one dimension and wide in the other dimension. The wide side creates an optically transparent viewing window. A camera and light source are placed relative to the viewing window, such that the camera is able to image gas bubbles and/or fibrin particles flowing within the liquid, e.g., dialysate stream, and through the optically transparent viewing chamber. The camera sends signals to a controller, e.g., processor and memory device, which determines the velocity of the bubbles or particles, and derives the velocity of the fluid from the bubble/particle velocities. Knowing the velocity of the dialysate and the cross-sectional area of the viewing portion, the system can then determine the flowrate of the dialysate. The system software is also configured to determine the shape and/or size of the object, which enables the system to determine whether the object is a gas bubble or fibrin particle for example.

The system can be configured with one or multiple light sources. Multiple light sources can be sequenced to improve feature illumination. The light source(s) can backlight the viewing portion, light the viewing surface from the front (same side as camera) or back, from one or more of the top or bottom of the viewing portion, or any combination thereof. Optics, e.g., lenses or mirrors, may be provided to focus or direct light from the source to a desired destination.

A second aspect of the present disclosure includes an improved cassette-based fluid or dialysate heater. The heater in one embodiment heats the fluid inductively, such that wires or electrical leads do not have to extend to the heating element and the element can contact the dialysate directly. The resulting heater efficiently enables its package to be small and suitable for cassette mounting. In one embodiment, a single housing is provided with a multi-pass element. In another embodiment, multiple housings are provided or a U-shaped housing with multiple legs is provided, each having at least one heater element.

A first embodiment of the present disclosure includes an improved system for medical fluid flowrate, particle and/or gas bubble detection. The system may be implemented in a medical fluid machine having: (i) an enclosure; (ii) a disposable unit accepted by the enclosure, the disposable unit including or communicating with a pathway through which a medical fluid can flow, wherein the pathway includes a viewing portion; (iii) a light source configured and arranged to emit light into the viewing portion of the tube; (iv) a camera focused on the viewing portion of the tube; (v) a processor or software configured to determine the presence, shape, and speed of particles entrained in the medical fluid based on at least two images of the particle in the viewing area taken by the camera; and (vi) alternatively or additionally, processor software configured to detect gas bubbles in the medical fluid, estimate the volume of same and accumulate total estimated volume of gas passing the detector (viewed portion of fluid pathway).

In one implementation, a medical fluid machine includes an enclosure; a disposable unit accepted by the enclosure, the disposable unit including a conduit through which a medical fluid can flow, the conduit including a viewing portion; a light source configured and arranged to emit light onto the viewing portion of the conduit; a camera focused on the viewing portion of the conduit; and a processor operable with the camera configured to determine a speed of a particle entrained in the medical fluid based on at least two images of the particle in the viewing area taken by the camera.

In one implementation, the disposable unit includes at least one characteristic selected from the group consisting of: (i) having an at least semi-rigid valve portion; (ii) having a flexible pumping portion; (iii) having a tube configured to operate with a peristaltic pump; (iv) having a flow path portion for the medical fluid to be heated; (v) having an air trap portion; (vi) the conduit being a rigid pathway formed in the disposable unit; and (vii) the conduit being a tube connected fluidly to the disposable unit.

In one implementation, the light source includes at least one characteristic selected from the group consisting of: (i) employing a light emitting diode ("LED") or laser diode; (ii) including multiple lights configured to illuminate the viewing portion from multiple angles; (iii) being positioned on a side of the viewing position that is at least substantially opposite from a side of the viewing portion that the camera is positioned; (iv) being positioned on a side of the viewing portion that is at least substantially the same as the side of the viewing portion that the camera is positioned; (v) being positioned on a side of the viewing portion that is at an angle with respect to a side of the viewing portion that the camera is positioned; (vi) being illuminated intermittently and in sync with when the camera is taking images of the viewing portion; and (vii) being a high intensity light source.

In one implementation, the light source is configured to be at least one of: (i) lighted sequentially when the light source includes multiple light emitting elements and (ii) positioned so that light reflecting off the viewing portion does not impinge the camera.

In one implementation, the camera includes at least one characteristic selected from the group consisting of: (i) having a frame rate of at least five hundred frames per second; (ii) being monochrome; and (iii) being capable of color imaging.

In one implementation, the viewing portion includes at least one characteristic selected from the group consisting of: (i) being formed in the conduit; (ii) being spliced into the conduit; (iii) being connected to the conduit; (iv) having a relatively high aspect ratio; (v) being at least substantially rectangular; (vi) being relatively thin; (vii) being configured so that the particle tends not to be masked by another particle; and (viii) having a known cross-sectional area.

In one implementation, the processor includes at least one characteristic selected from the group consisting of: (i) being configured to determine at least one of a quantity, size, type and velocity of the particle in the medical fluid; (ii) being configured to determine at least one of the speed, velocity and the volumetric fluid flowrate of the medical fluid; (iii) being a digital signal processor; and (iv) being operable with an assumption that the particles are distributed across the entire cross-section of the viewing portion.

In one implementation, the machine includes an apparatus configured and arranged to induce vibrations into the medical fluid flowing through the viewing portion.

In one implementation, a medical fluid machine includes: a fluid carrying unit including a conduit through which a medical fluid can flow, the conduit including a viewing portion; a light source configured and arranged to emit light onto the viewing portion of the conduit; a camera focused on the viewing portion of the conduit; and a processor operable with the camera and configured to determine that a particle entrained in the medical fluid is an air bubble based on a determined shape of the bubble.

In one implementation, the fluid carrying unit is disposable.

In one implementation, the determined shape for an air bubble is an at least substantially circular or rectangular shape.

In one implementation, the processor is configured to determine that the particle is an air bubble when a reflected highlight indicative of a spherical shape is detected by the camera.

In one implementation, the processor is configured to determine that a particle entrained in the medical fluid is an acceptable therapy particle when a determined shape of the particle is irregular.

A second embodiment of the present disclosure includes an improved medication fluid machine having a pump that pumps medical fluid and a heater that heats the fluid, the heater including an electrically insulative housing, at least one conductive sheet of material suitable for contacting medical fluid disposed within the housing, the sheet defining a fluid flow path that changes the direction of the fluid at least one time, and a primary coil of a transformer located outside the housing, the primary coil configured to induce a current into the at least one conductive sheet, causing heat to be transferred to the fluid.

It is therefore an advantage of the present disclosure to provide an improved apparatus and method for detecting medical fluid flowrate.

Another further advantage of the present disclosure is to provide an improved medical fluid heater.

Additional features and advantages of the present disclosure are described in, and will be apparent from, the following Detailed Description of the Disclosure and the figures.

BRIEF DESCRIPTION OF THE FIGURES

FIGS. 4 and 5 are perspective and front elevation views, respectively, of one embodiment of an inductive disposable-cassette mountable dialysis fluid heater.

DETAILED DESCRIPTION

The present disclosure relates to medical fluid delivery systems that employ a pump, such as a peristaltic pump. In particular, the present disclosure provides systems, methods and apparatuses for cassette-based dialysis therapies including but not limited to hemodialysis, hemofiltration, hemodiafiltration, any type of continuous renal replacement therapy ("CRRT"), congestive heart failure treatment, CAPD, APD (including tidal modalities) and CFPD. The cassette is disposable and typically discarded after a single use or therapy, reducing risks associated with contamination.

Product Configurations

Referring now to FIGS. 1A to 1F a first configuration for the components of system 10 is illustrated by configuration 350. As discussed herein, in one embodiment the pumping technology used for system 10 is a peristaltic pump. It is expressly contemplated, however, that many features and embodiments discusses herein can be used with peristaltic pumps, volumetric pumps, pumps operated pneumatically, pumps operated mechanically, pumps operated hydraulically and any combination thereof. The component features discussed in connection configuration 350 and indeed in connection with configurations 370 and 390 shown in connection with FIGS. 2A to 2F and 3A to 3F, respectfully, are applicable to any of the different types of pumping technologies just previously described. Indeed, while cassette 50 is shown in connection with each of configuration 350, 370 and 390.

Figure 1C:
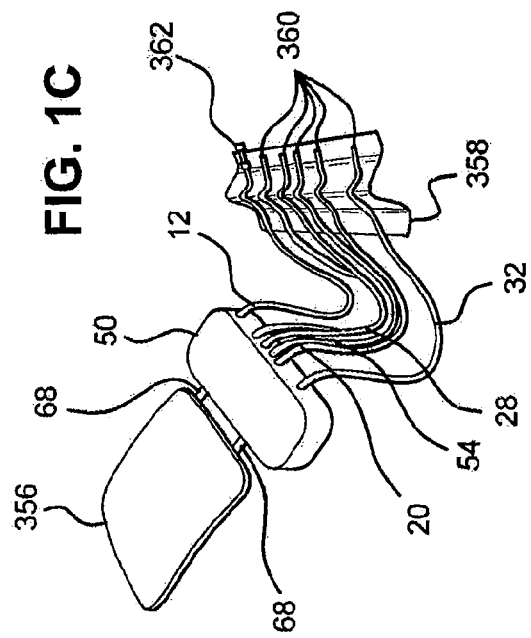
FIGS. 1A to 1F are perspective views illustrating different components of one configuration of a dialysis system employing the embodiments discussed herein.
Figure 1B:
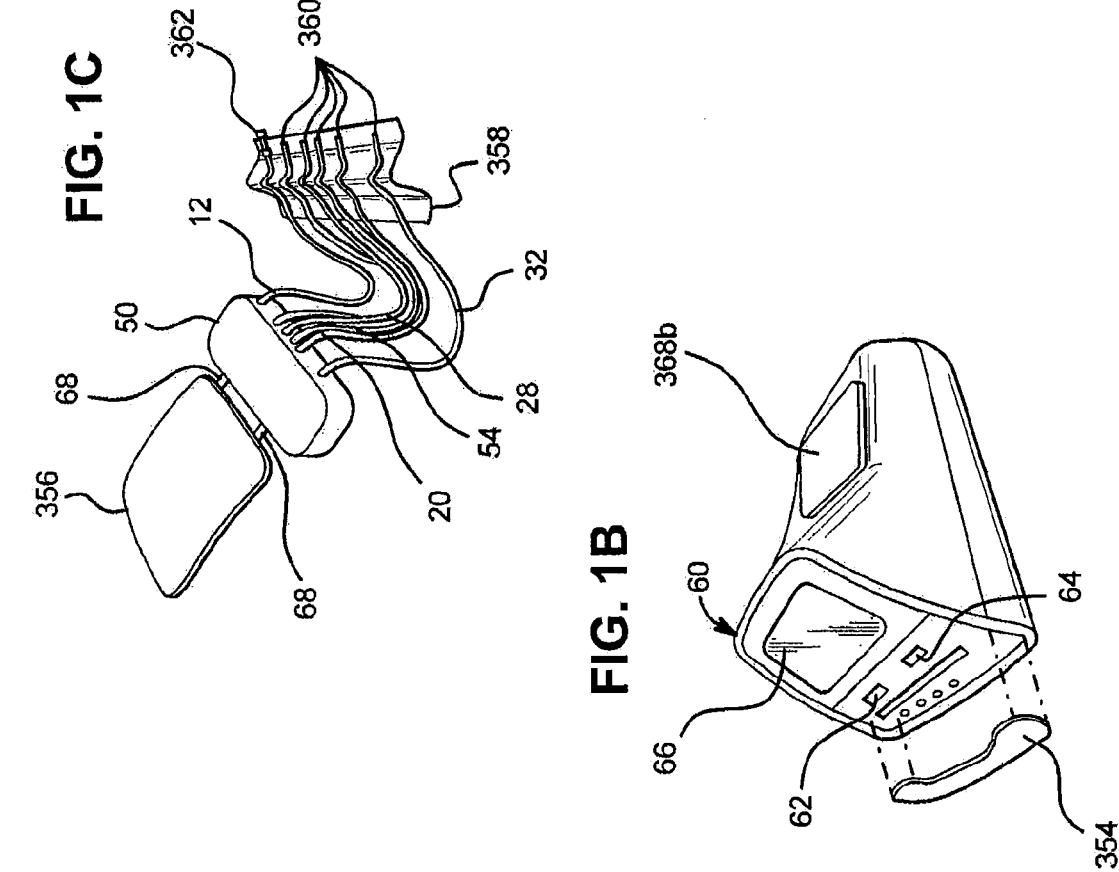
Figure 1A:
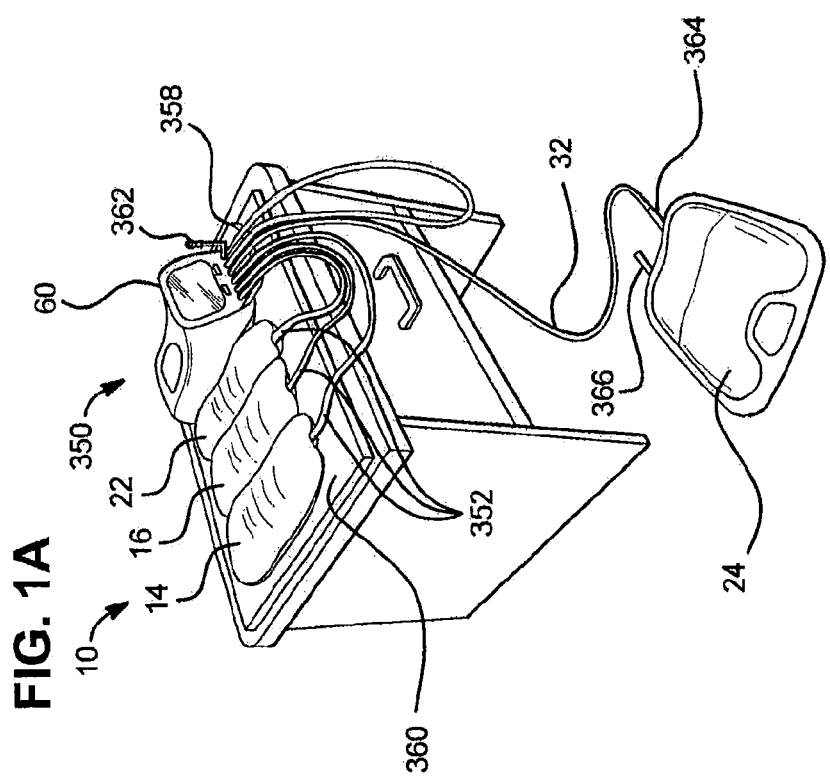

As seen in FIG. 1A, configuration 350 of system 10 includes supply bags, 14, 16, and 22 and drain bag 24. Those bags are connected fluidly to machine or unit 60 via lines 28, 54, 20 and 32, respectfully, as seen in FIG. 1C additionally. FIG. 1A further illustrates that configuration 350 of system 10 includes an organizational mat 352, which is shown and discussed in more detail in connection with FIG. 1F. FIG. 1A further illustrates that configuration 350 can be placed partly on a desk or nightstand, with drain bag 24 being placed on the floor. In the illustrated embodiment, supply bags 14, 16 and 22 and cassette 50 are loaded and maintained in an at least substantially horizontal configuration.

Referring now to FIG. 1B, machine or unit 60 is illustrated in more detail. Here, unit 60 is a single integrated device, which includes a horizontal front drawer 354, the back of which curves vertically, so that a portion of cassette 50 is turned vertically for air separation purposes. Cassette 50 and heater bag 356, shown in more detail in connection with FIG. 1C, are loaded via drawer 354 simultaneously into unit 60. Drawer 354 also aids in organizing cassette 50 and heater bag 356 to aid the patient in aligning, inserting and removing those items. To that end, the identification of the separate lines 28, 54, 20 and 32 is also shown on drawer 354, so that the patient can match corresponding indicia on the lines with the markings on drawer 354 for proper cassette installation. In the illustrated embodiment, display 66 of machine or unit 60 is tilted at an angle of about forty-five degrees to about sixty degrees from vertical for ready viewing. Other angles could also be used. Unit 60 also includes controls 62 and 64, which can be off-screen controls, such as membrane switches, or on-screen controls, such as a touch screen overlay.

Referring now to FIG. 1C, the disposable, sterile, fluid carrying portion of configuration 350 is illustrated. The disposable set includes cassette 50 and separate heater bag 356, which are connected together via heater tubes. Thus, in configuration 350, heater 38 is located inside machine 60. As discussed above, unit 60 cooperates with drawer 354 to turn a portion of heater bag 356 upwards for air separation. In the illustrated embodiment, heater bag 356 is loaded first via drawer 354 into unit 60. The distill or free end of heater bag 356 is turned upward. That end may contain a vent or a filter, such as a hydrophobic membrane, which enables air escaping from the fluid in the heating pathway to collect at the vertical upper end of heater bag 356 and to eventually be vented through such a vent or filter.

The disposable set includes a tubing organizer 358, which can be placed on the table or night stand to further assist the loading of cassette 50 and heater bag 356. Organizer 358 holds supply lines 28, 54 and 20 next to one another. Those lines in an embodiment are tacked or otherwise held together, so that the patient knows that those lines are intended to be connected to supply bags 22, 16 and 14, respectively. Drain line 32 in an embodiment has a larger diameter hose than do supply lines 28, 54 and 20. This also helps the patient to keep the different lines straight in memory. Thus it should be appreciated that in configuration 350, cassette 50 and the lines connected to organizer 358 are loaded through the front of the unit 60, which places the tubes in an advantageous viewing area in front of the patient.

The identification of supply lines 28, 54 and 20, drain line 32 and patient line 12 is further aided via identifying markings. For example, clamps 360 (FIG. 1C) located at the distil ends of supply lines 20, 54, and 28 and drain line 32 are color-coded. Furthermore, the clamps can have molded line identification or indicia. Patient line 12 is identified via a connector 362 at its distil end. Connector 362 is removably fixed to unit 60 as seen in FIG. 1A for priming. Unit 60 in one embodiment has a sensor, which senses whether connector 362 of patient line 12 is in proper position for priming before allowing therapy to begin.

Figure 1E:
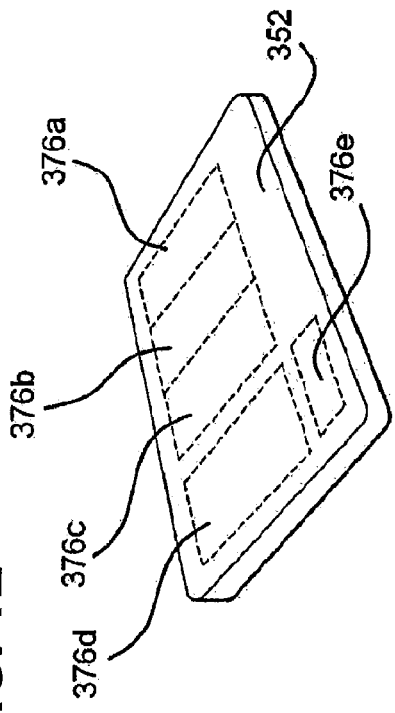
Figure 1F:
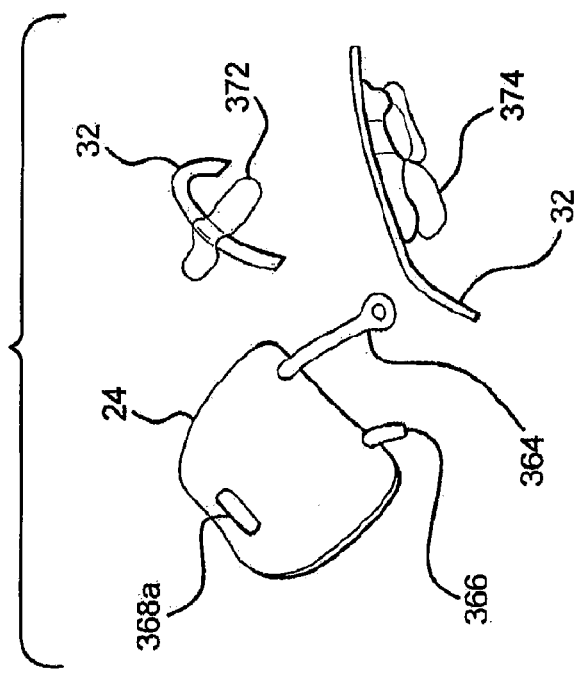
Figure 1D:
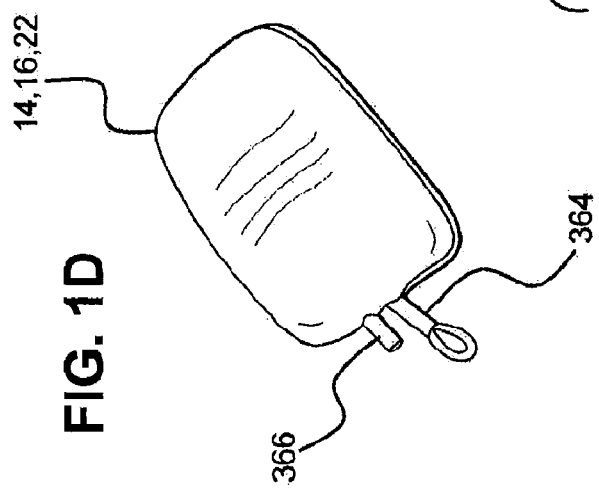

As seen in FIG. 1D, supply bags 14, 16 and 22 each include a port 364 and a vent 366. Vent 366 for example includes a filter or a membrane, such as a hydrophobic membrane, which enables gas to be purged from the supply bags. Ports 364 each include a seal, which is spiked via the ends of supply lines 28, 54 and 20. The seal eliminates the need for a clamp on supply bag port 364.

Referring now to FIG. 1E, an embodiment for drain bag 24 is illustrated. Drain bag 24 also includes a port 364 and vent 366 as described above in connection with FIG. 1D. Bag 24 also includes a handle 368a, which aids in carrying bag 24 when it is full of spent fluid. A handle 368b is also provided with machine 60 as seen in connection with FIG. 1B for its ready transport. As seen in FIG. 1E, drain line 32 is provided with one or more apparatus, which enables the drain line to be fixed and held in a desired position. For example, drain line 32 can be provided with a flexible, adhesive-backed strip 372, which may enables the drain line to be adhered to the desk or night stand, for example. Strip 372 in an embodiment slidably engages drain line 372 in frictional manner, so that strip 372 can be moved along drain line 32 to a desirable position. Additionally or alternatively, a clamp 374, which can be reusable, is provided so that drain line 32 can be clamped in a desirable position. Clamp 374 slides over drain line 32 and in embodiment can be positioned frictionally along different areas of the drain line.

As seen in FIG. 1F, organizational mat 352 includes indicia 376a to 376e, which identifies the component at the illustrated location and where a component, such as the supply bag and drain bag, should be located. Mat 352 is reusable and made of a washable material. The indicia can further include written instructions, reminders and other useful information, such as color codes for the clamps and lines.

Flowrate Detection Apparatus and Method

As discussed above, it is desirable for the peritoneal dialysis systems described herein to be able to measure dialysate flowrate accurately and to detect and quantify gas bubbles and solid particles flowing through a conduit, which can for example be coupled to a disposal dialysis cassette, such as cassette 50 of system 10. Additionally or alternatively, it is desirable to detect and qualify same for dialysate or medical fluid flowing through the cassette itself. FIGS. 2A, 2B, 3A and 3B illustrate systems 450 and 470, respectively, which detect dialysate flowrate, and quantify the size and/or shape of particles in dialysate, such as gas bubbles or fibrin particles. The systems are intended to be able to differentiate between different types and/or shapes of particles and can operate with dialysis and drug infusion systems alternatively.

Figure 2A:
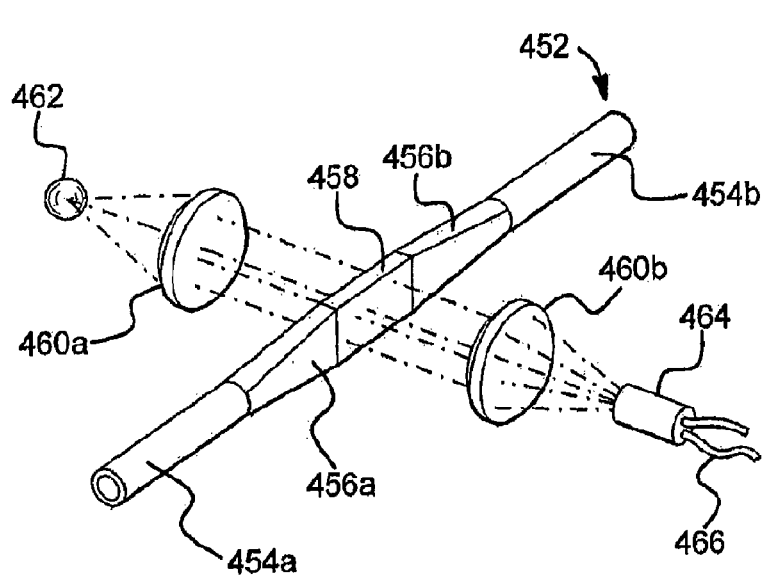
FIGS. 2A and 2B are perspective views of two embodiments for a dialysate flowrate, gas bubble and fibrin particle detection system.

System 450 of FIG. 2A includes a tube or conduit 452, such as an optically transparent tube or conduit. Tube or conduit 452 can be any conduit used in a peritoneal dialysis system, such as one of the supply tubes 20, 28 and 54, drain tube 32 or patient tube 12 described herein. Tube or conduit 452 is alternatively provided as a part of a disposable cassette, such as cassette 50 described herein.

In the illustrated embodiment, tube or conduit 452 includes ends 454a and 454b, which are at least substantially circular in cross-section. Ends 454a and 454b extend to transitional sections 456a and 456b, respectively. Transitional sections transition from the generally circular cross-section of ends 454a and 454b to the at least substantially rectangular cross-section of a viewing portion 458 of tube 452. The cross-sectional area of viewing portion 458 is known. In an alternative embodiment (not illustrated) viewing portion 458 is provided as a rectangular and optically transparent, e.g., rigid pathway of a disposable cassette, such as cassette 50.

The shape of the viewing portion 458 of tube or pathway 452 is chosen to ensure that any particles traveling in the dialysate or fluid can be imaged clearly by camera 464. Viewing portion 458 can be formed integrally with conduit 452, spliced into conduit 452 or connected to the end of the conduit. The illustrated rectangular viewing window is intended to have an aspect ratio approximately equal to that of the camera detector. A cross-sectional shape having a high aspect ratio, such as the illustrated rectangular shape is desirable. The high aspect ratio shape enables a camera 464 to look through a relatively thin section of dialysate flow. This thinned section of flow reduces the number of particles that can be hidden from view because they reside behind particles nearer to camera 464.

Optics or lenses 460a and 460b are placed on either side of viewing portion 458 in system 450 of FIG. 2A. The optics or lenses 460a and 460b in an embodiment are convex lenses constructed of any suitable material, e.g., plastic or glass that is optically transparent to the wavelength of light from the light source 462. Lens 460b is positioned between viewing portion 458 and camera 464. Lens 460a is positioned between viewing portion 458 and a light source 462 and is designed to collimate the light from the light source 462. Light source 462 can be any suitable light source, such as a light emitting diode ("LED") or a laser diode, which improves the depth of the field.

Light source 462 illuminates the gas bubbles or particles within the fluid or dialysate, so that the bubbles or particles can be viewed by camera 464. Lens 460b is configured to focus the viewing area 458 onto the image detector of the camera 464. An aperture (not shown) between the focusing lens 460b and the camera may be included to increase the depth-of-field view of the camera so that the entire volume of fluid inside the viewing portion 458 is in focus. Alternatively, the diameter of lens 460b may be chosen so as to provide the appropriate aperture effect to obtain the required depth of field.

Figure 2B:
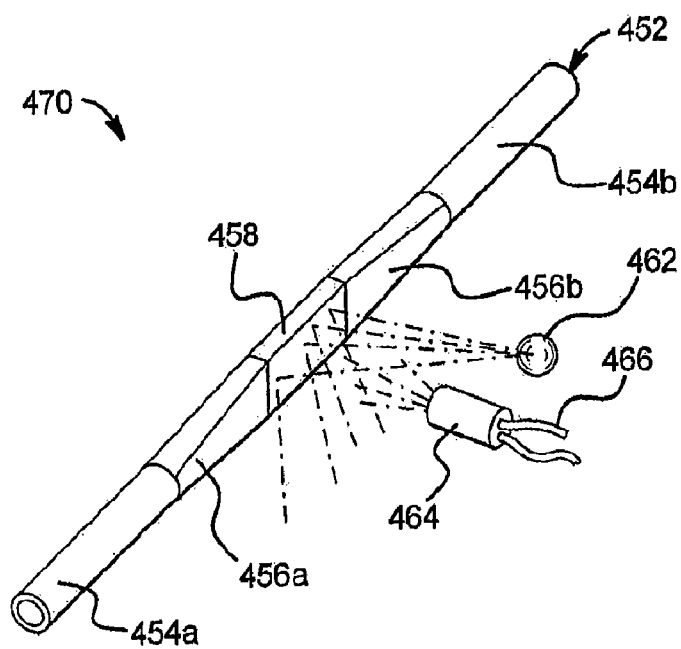

Referring now to FIG. 2B, alternative system 470 for detecting flowrate, particle quantity, particle size and shape is illustrated. System 470 includes many of the same components described above in connection with system 470, such as tube or conduit 452 having ends 454a, transitional portions 456a and 456b, and inner viewing portion 458. Inner viewing portion 458 can have an at least substantially rectangular cross-sectional shape, for example, with a high aspect ratio creating a relatively thin area, which tends to preclude obstruction of gas bubbles or particles relative to camera 464. As seen in system 470, lenses or optics 460a and 460b are not provided. In an alternative embodiment, those optics are provided. Furthermore, it may be possible to eliminate optics 460a and 460b from system 450 of FIG. 2A.

The primary difference between system 470 and system 450 is that light source 462 is placed on the same side of conduit 452 as is camera 464. This configuration illuminates the particles or gas bubbles from the front relative to camera 464 as opposed to the back-lighting of system 450. With either system 450 or 470 it is desirable however that the side that camera 464 views is optically transparent, smooth, and/or mirror-like. As seen in FIG. 2B, for front lighting system 470 it is desirable that light from source 462 is reflected by the mirror-smooth viewing window away from camera 464 entirely, so that only the particles of interest inside the viewing chamber scatter the light back to the camera. It is also desirable that light source 462 not reflect back into camera 464. This is analogous to attempting to photograph a picture through its glass frame using a flashbulb. If the camera can "see" the reflection of the flash, then the flash can blind the picture of interest. It is desirable therefore to position camera 464 to one side or use a light source 462 not attached to camera 464, so that camera 464 does not "see" the reflection of light source in viewing area 458.

In an alternative embodiment, multiple light sources 462 are placed in the front of viewing portion 458 relative to camera 464, so that the light can be directed to the surface of viewing portion 458 via multiple angles, and/or sequenced as described above. Although not illustrated, it is possible to light viewing portion 458 from its top and/or bottom surface as desired. Further, any combination of back lighting, front lighting and/or top and bottom lighting may be provided as needed to optimize performance and cost. One advantage of system 470 for example is that the hardware apparatuses 462 and 464 can be located on a single side of the dialysis machine, for example unit 60, so that the opposing surface of the cassette can be located at or near the edge of the unit. The one or more light source 462 is positioned such that its light does not impinge the camera.

Figure 3A:
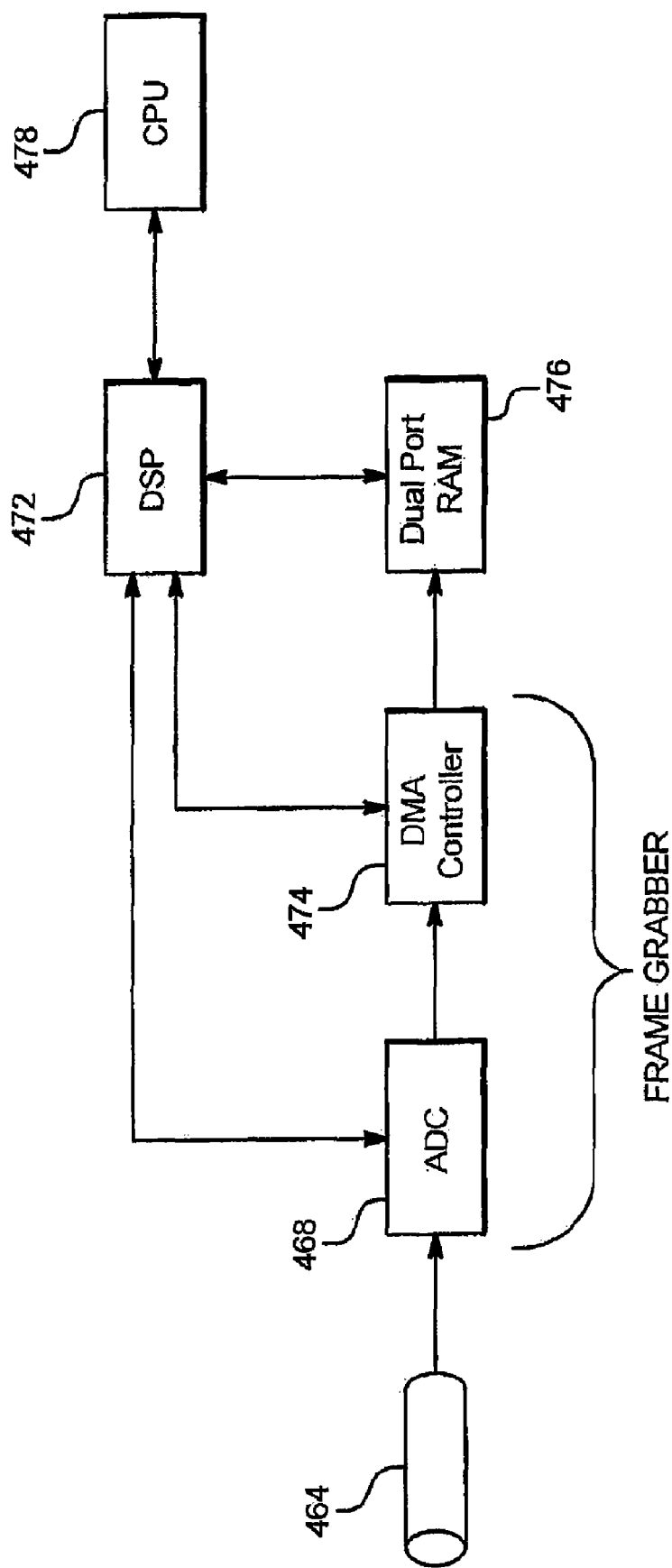
FIG. 3A is a schematic illustrating one embodiment of a system for the dialystate flowrate, gas bubble and fibrin particle detection system of FIGS. 2A and 2B.

Referring additionally to FIG. 3A, in systems 450 and 470, camera 464 can be a small monochrome or color camera utilizing charge coupled device ("CCD") or complementary metal oxide semiconductor ("CMOS") sensor technology. The frame rate of systems 450 and 470 is set to coincide with the maximum expected flowrates. In one embodiment, camera 464 utilizes a frame rate of about one thousand frames per second or higher. This requires digital signal processor ("DSP") 472 to be a high speed DSP. An analog to digital ("ADC") converter 468 converts an analog output of camera 464 to a digital signal, which is sent for example via wires or leads 466 (FIGS. 2A and 2B) to processing electronics including a microprocessor and/or digital signal processor ("DSP") 472. In one embodiment, a commercially available frame grabber includes an on-board ADC 468 and a DMA controller 474, which transfers image data to and from DSP 472 and a dual port random access memory ("RAM") 476. RAM 476 stores software and buffers data. DSP 472 processes the data using the software and communicates with a central processing unit ("CPU") 478. CPU 478 operates with other controllers within dialysis machine 60, such as a pump controller, which CPU 478 can direct to shut down the pump upon a signal from DSP 472 that air has been detected.

All associated electronics including camera 464 are provided on a single printed circuit board in one embodiment. Memory 476 stores code or software, which as described below recognizes the particles or bubbles, determines the velocity of same, determines the velocity of the liquid from the velocity of the particles, and determines the volumetric flowrate using the velocity of the liquid in combination with the known cross-sectional area of view portion 458.

The limited exposure time of camera 464 makes a high intensity light source desirable. Accordingly, in an embodiment, light source 462 is a high intensity light emitting diode ("LED"). Processor 472 can be configured such that light source 462 is energized only when camera 464 is activated. Intermittent light source activation enables light source 462 to withstand a higher peak current and corresponding higher brightness than if light source 462 is powered continuously. LED's are inherently highly reliable if properly applied, and a backup may not be needed. Systems 450 and 470 may or may not need a white LED (if a monochrome camera sensor is used). High intensity LED's or infrared ("IR") LEDs are likely sufficient for the intensity of light needed.

Systems 450 and 470 can also provide multiple light sources (and possibly multiple lenses 460a) to illuminate viewing portion 458 from multiple angles. Here, each light source can be activated sequentially in time with sequential frames of camera 464 and/or simultaneously for each camera frame.

In a further alternative embodiment, a small transducer (not illustrated) is provided, which induces ultrasonic or other frequencies into the fluid flow. The frequencies can be modulated and multiple different frequencies can be induced into the flow. A vibration causing device, such as a piezoelectric or pressure wave causing transducer causes vibrations to be made to tube or conduit 452 directly or to the fluid within conduit 452 to help prevent bubbles or particles from sticking to the inner wall of conduit 452 and/or to each other. The transducer optimally induces the vibrations directly to viewing portion 458. The transducer and the other apparatuses of systems 450 and 470, such as light source 462, lenses 460a and 460b, camera 464, processor 472 and memory 476 are each provided in one embodiment in the peritoneal dialysis instrument or actuator unit.

Figure 3B:
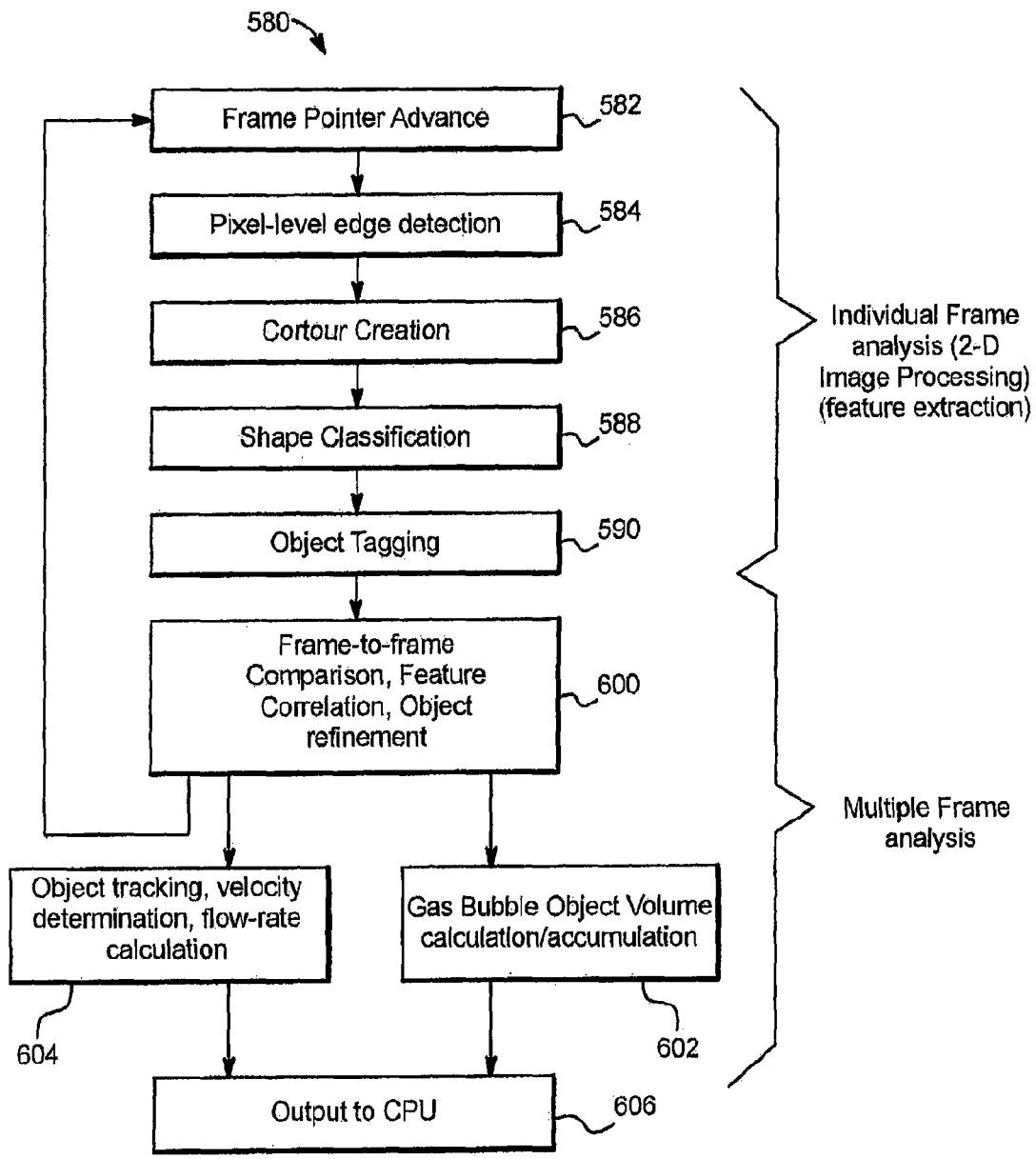
FIG. 3B is a schematic flow diagram illustrating one embodiment of an algorithm for individual frame analysis including two dimensional image processing and feature extraction and multiple frame analysis for the dialystate flowrate gas bubble and fibrin particle detection system of FIGS. 2A and 2B.

Referring additionally to FIG. 3B, flow chart 580 illustrates that systems 450 and 470 have at least one and possibly two major functions, namely (i) individual frame analysis including two dimensional image processing and feature extraction and (ii) multiple frame analysis. RAM 476 stores software that is configured to detect, count, measure and track the individual particles or bubbles flowing within the dialysate or fluid as the objects pass through the field of view of viewing portion 458. The software in an embodiment is configured to distinguish between different shapes, e.g., between at least substantially spherical gas bubbles and non-uniform particles, e.g., fibrin particles. In this way, the software and thus systems 450 and 470 can distinguish between gas bubbles and other types of objects. The software can also determine the velocity of the particles and thus the velocity of the fluid by taking two or more pictures, determining the distance traveled by one or more of the particles, averaging the distances in one embodiment, and dividing the distance (e.g., average distance) by the time between exposures.

With individual frame recognition, hardware-based framegrabber 468/474 stores image frames sent via camera 464 into RAM buffer 476 in rapid succession, as seen in connection with block 582. DSP 472 and RAM 476 process each frame using edge-based shape detection at the pixel level, as seen in connection with block 584. From the edge features, DSP 472 and RAM 476 develop object contours, as seen in connection with block 586, with which a pattern recognition algorithm stored on RAM 476 performs shape classification, e.g., into either a circular or non-circular classification, as seen in connection with block 588. Each object is then tagged with a unique identification that includes the object's classification (e.g., gas bubble or fibrin) and size, as seen in connection with block 590. Thus, individual frame recognition can be used for example to detect gas in the system.

In the multiple frame analysis, systems 450 and 470 perform frame-to-frame comparison to correlate features and refine object shape and size as seen in connection with block 600. For object detection, frame-to-frame comparison brings a three dimensional aspect to object detection. For example, non-symmetrical fibrin particles will change shape as they rotate within a dialysate stream. Spherical gas particles do not change shape significantly as they rotate within the dialysate stream. Using multiple frames, systems 450 and 470 can look for shape changes to confirm a classification made from an earlier frame. Further, systems 450, 470 can include additional particle type identifying features, such as the ability to look for highlights on an illuminated object. For example, systems 450, 470 can look for reflections on a spherical gas bubble that may not appear on other types of particles, such as fibrin.

The integration of multiple images allows systems 450 and 470 to distinguish overlapping objects assuming that they do not overlap the entire time they are in the field of view. This helps in determining how many, e.g., gas particles there are, know the volumes of gas, and calculate a total amount of gas, as seen in connection with block 602. To this end, system 450, 470 classifies all objects found to be circular or spherical as possible gas bubbles. From the visible diameter, the volume of each bubble is calculated. The volumes of all gas bubble objects are accumulated to provide a measure of the total gas volume passing through the chamber. It should be appreciated that in many applications, a small amount of gas, e.g., one-hundred milliliters, over a period of time or for a particular volume of fluid is allowable. An air alarm condition in one embodiment is therefore based on a set amount of accumulated air.

In determining total gas volume in this manner, it should be appreciated that systems 450 and 470 are dependent on particle density. That is, as the density of objects in the fluid increases, the likelihood that certain objects will be misidentified or not seen due to overlap increases.

As seen in connection with block 604, systems 450 and 470 provide methods and apparatuses that measure the quantity, size, shape and velocity of particles or gas bubbles flowing within a fluid, such as dialysate. Determining the velocity of particles moving with the fluid allows the velocity of the fluid itself to be determined, that is, the two are assumed to be equal. Knowing the cross-sectional area of viewing portion 458 in combination with the fluid velocity enables systems 450 and 470 to calculate the volumetric flowrate of the dialysate. If only flowrate is needed, feature tracking is performed and high particle count is not an issue.

Knowing the flowrate over time yields total volume of fluid delivered. System 450, 470 can further increase total volume accuracy by subtracting a total gas volume from a total calculated volume to obtain a total liquid volume.

If possible, system 450, 470 tracks all visible objects as they move across the field of view. The systems analyze the contribution to fluid flow of each pixel-mapped location of the viewing chamber 458. This information is known to the software, so that a "contribution factor" is given to each object's velocity based upon its two dimensional position for calculating the overall fluid flow.

Systems 450 and 470 output information to the CPU 478 of dialysis machine 60, as seen in connection with block 606, which communicates with and controls other systems within machine 60. One main purpose of systems 450 and 470 for machine operation is the detection of air in the dialysis system. For this, systems 450 and 470 rely on the detection of the shape of the particles entrained in the dialysate as discussed above. If uniform or at least substantially spherical particles are detected, system 450 or 470 assumes that gas or air has entered the system, causes CPU 478 to sound and/or display an alarm any other to take any other appropriate action, such as shutting down the pumping of dialysate to the patient.

Conversely, if systems 450 and 470 see only fibrin or other body particles, the systems are programmed to assume that non-uniform, non-spherical particles are not gas bubbles in a non-alarm condition. Here, systems 450 and 470 can be used to perform flowrate calculations and send flowrate information to CPU 478, which uses this information for display to the patient and/or for pump speed feedback.

Systems 450 and 470 can be applied to fluids other than dialysate, in which the proportion of particles or bubbles is not too great, e.g., for partical/bubble differentiation and quantification. In fact, optical systems 450 and 470 may be utilized with dry particle "fluids", e.g., dry sand, assuming the mechanical vibration discussed above is sufficient to keep the sand moving in a fluid-like manner, and that the particle sizes are not too small to be distinguished. It is also contemplated to use systems 450 and 470 with gas fluid streams, such as compressible gases. Here too, the systems rely upon the assumption that the particles or other discernable matter carried by the compressible gas stream travel at least substantially at the same rate as the gas.

As mentioned, at least the conduit portion 452 of systems 450 and 470 is adapted readily to be provided in a sealed, low cost disposable cassette, such as cassette 50. Alternatively, conduit portion 452 of systems 450 and 470 is a permanent or semi-permanent component of systems 450 and 470

Inductive Heaters

Referring now to FIGS. 4 to 13, various embodiments for inductive, inline dialysate heaters are illustrated. FIGS. 4 and 5 illustrate a first embodiment via heater 480. Heater 480 in one embodiment is operable with a disposable cassette, such as cassette 50 described for use with system 10. Heater 480 in an embodiment is located externally. Alternatively, heater 480 is incorporated directly into a cassette. In either case, it is contemplated to place heater 480 upstream of the pump in one embodiment to help reduce the need to compensate for fluid temperature when determining pumping accuracy.

Heater 480 in the illustrated embodiment is a relatively small, multi-pass, disposable, inductive heater configured to heat dialysate, for example, from about 5° C. to about 37° C. (body temperature) at a dialysate flowrate of about 200 ml/min. Heater 480 includes a housing 482, such as a plastic or otherwise electrically insulative housing. Suitable materials for housing 482 include plastics approved for carrying injectable fluids. Housing 482 has a top wall 484, sidewalls 486 and 488, a bottom wall 490 and front and back walls (not seen). In the illustrated embodiment, heater 480 defines or includes a fluid inlet 492 and a fluid outlet 494. Metal or conductive plates or baffles 496a to 496d are located within the housing. The plates 496 (referring collectively to plates 496a to 496d) define a tortuous path for the dialysate to flow from the inlet 492 to the outlet 494. The illustrated embodiment shows four plates, but more or less plates may be used as desired. Plates 496 can have flow restricting baffles.

In one implementation the plates are heated to 47° C. to achieve the above-described desired fluid heating. Changing the number of plates 496 or total surface area of same would raise or lower the necessary plate temperature. The illustrated housing 482 is generally rectangular but could have a different shape. The aspect ratio or length l versus depth d of plates 496 can be varied as needed. As mentioned above, housing 482 may be incorporated into a disposable cassette (e.g., cassette 50) or operate upstream or downstream from the cassette. Plates 496 can be made from any of a variety of medically suitable metals, e.g., stainless steel, as desired to enhance the inductive heating of the plates. Plates 496 are covered with a protective plastic film in one embodiment allowing for better conducting metals to be used to form plates 496.

Plates 496 form a secondary coil of a transformer shown in more detail below in connection with electrical system 540 of FIG. 13. The primary coil of the transformer can be integral to the unit 60 and reusable. Unit 60 is configured such that the inductive heater portion of the disposable cassette is positioned onto or adjacent to the primary coil located within unit 60. When energized, the primary coil induces a current into the shorted secondary coil (e.g., plates 496), heating the secondary, which in turn heats the inline flowing fluid. The primary and secondary coils are provided alternatively independently of the disposable cassette. Here, heater 480 is inserted independently onto the primary coil of the transformer, which can still be located within unit 60. Still further alternatively, the primary coil of the transformer is located external to unit 60.

One set of suitable dimensions for induction inline heater 480 is as follows. The dimensions are provided for illustration purposes only and are not intended to limit the scope of the disclosure in any way. The dimensions do demonstrate however that the inductive heater can be relatively small and is well-suited for incorporation into a disposable cassette. Again, the dimensions are sized in one embodiment to provide a heater 480 with the capacity to bring dialysate stored at about 5° C. to a therapy temperature of about 37° C., assuming a flowrate of about 200 ml/min. along a fluid pathway 498. To accomplish this requirement for the below-described dimensions, it is estimated that the temperature of plates 496a to 496d will need to be heated to about 47° C.

In the illustrated example, the length l and depth d of top 484 and bottom 490 of heater 480 is about 3.08 inches (7.82 cm) by 0.630 inches (1.60 cm), respectively. The height h of sidewalls 486 and 488 (and the front and back walls, not illustrated) is about 0.440 inch (1.12 cm). The thickness, t1, of top wall 484, sidewalls 486 and 488 and bottom wall 490 is about 0.065 inch (1.15 cm). The thickness of the non-illustrated front and back walls in an embodiment is the same as thickness t1.

The thickness t2 of heating plates 496a to 496d in one embodiment is about 0.04 inch (1.02 mm). Plates 496 as mentioned above are made in one embodiment of stainless steel, such as stainless steel 304 or 316. Plates 496 can be made of other suitable, non-corrosive, medically compatible, inductively heatable material, such as stainless steel 304, 316 or 430. The plates used for the above-described dimensions l, h and d for housing 482 are about 2.85 inches (7.24 cm) long by 0.500 inches (1.27 cm) deep in one embodiment. Plates 496a to 496d can be spaced apart from each other and from top wall 454 and bottom wall 490 a gap distance g of about 0.03 inches (0.762 mm). The spaces s left between the ends of plates 496a to 496d and the inner surfaces of sidewalls 486 and 488 is 0.100 inch (2.54 mm) in one embodiment. While gaps g, thicknesses t1 and t2, and spaces s are each described as being the same or constant, it is contemplated to vary one or more of those dimensions as needed. It is also expressly contemplated to provide a filter and/or a trap to remove any particles from the dialysate before the dialysate enters heater 480 to preserve the free flow of fluid through relatively narrow pathway 498.

The dimensions of inlet 492 and outlet 494 can be for example 0.250 inch (6.35 mm) inner diameter and 0.275 inches (6.99 mm) long, with a wall thickness of 0.065 inch (1.65 mm). Inlet 492 and outlet 494 can have flanged or integral ferrel-type apparatus to connect seelingly to heater lines 68 for example or with internal tubes disposed within disposable cassette 50. Inlet 492 and outlet 494 are formed alternatively integrally with one or more passages of a cassette.

In the illustrated embodiment, inlet 492 is located elevationally above outlet 494. This is advantageous in one respect because air or gas coming out of solution while being heated along pathway 498 tends to rise toward the top of heater 480 along gaps g, leaving at least substantially pure heated fluid or dialysate flow from the bottom of heater 480 through outlet 494. In an alternative embodiment, heater 480 is rotated ninety degrees from the orientation shown in FIGS. 4 and 5, so that plates 496 are disposed vertically. Inlet 492 can be horizontally disposed. Outlet 494 can be horizontally disposed or disposed downwardly and in communication with pathway 498 between plate 496d and wall 490. Gas digression from solution flowing along vertical plates 496 rises to the top of heater 480, causing at least substantially air-free dialysate to leave outlet 494.

Inline heater 480 eliminates the need for warmer bags 350 and 400 described above. In any of the orientations discussed above, inline heater 480 can include a separate air separation chamber or other air/gas purge apparatus, for example, as part of cassette 50. Heater 480 can also be provided with a hydrophobic membrane or a separator post having same for air/gas purging purposes.

Figure 6:
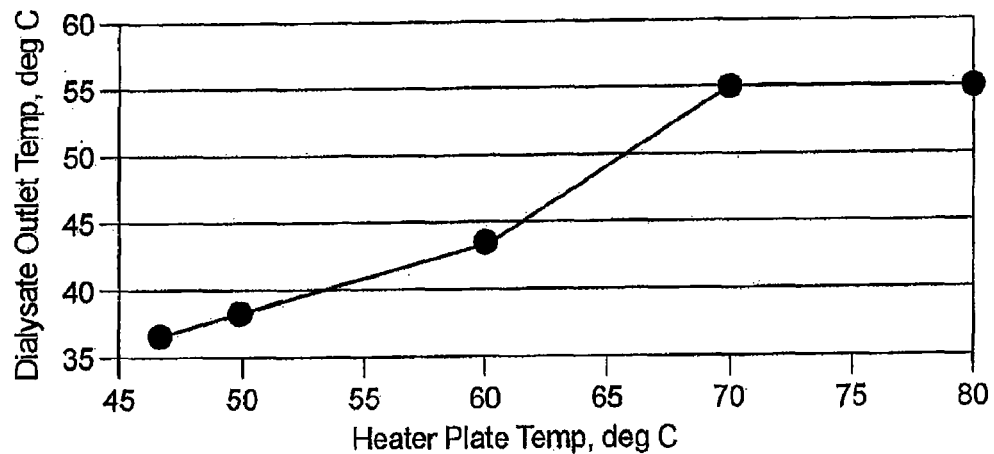
FIGS. 6 to 8 are charts showing various performance characteristics of the inductive fluid heater of FIGS. 4 and 5.
Figure 7:
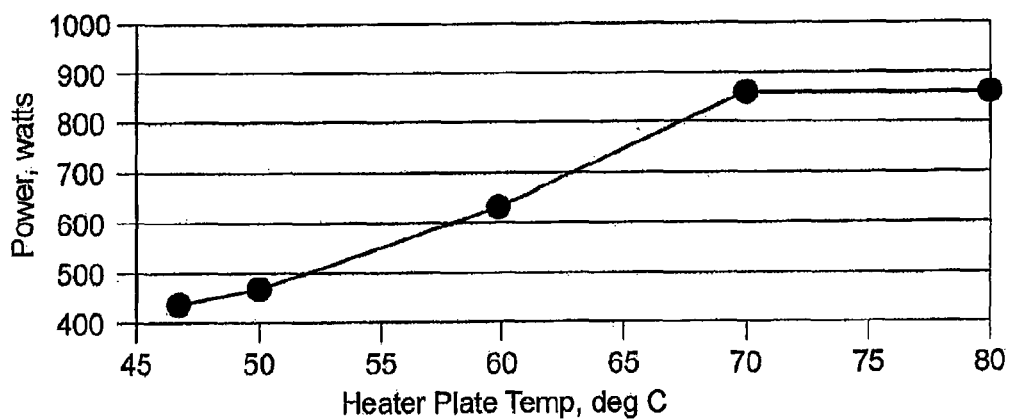
Figure 8:
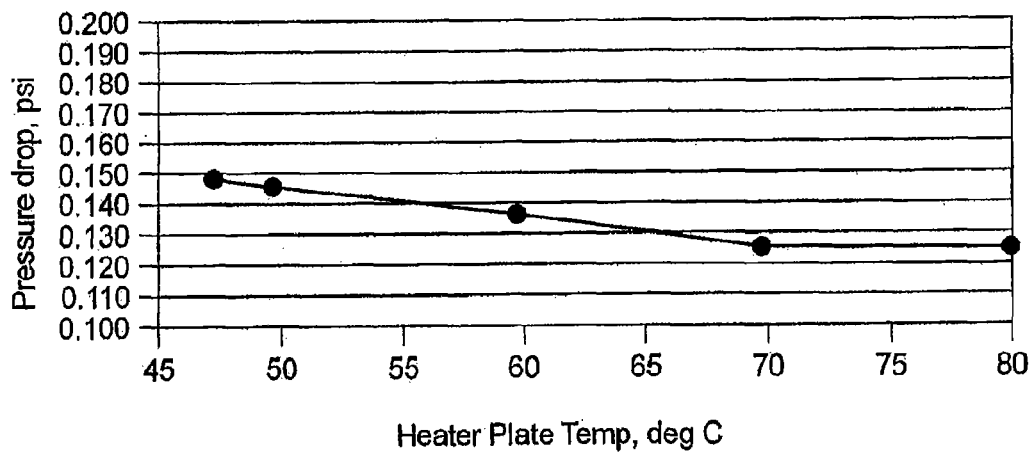

Referring now to FIGS. 6 to 8, various performances curves or charts for inline, inductive heater 480 are illustrated. The charts again apply to dialysate flowing at a rate of about 200 ml/min, which is being from about 5° C. to a desired temperature of about 37° C. FIG. 6 illustrates that heating plates 496a to 496d to a temperature of about 47° C. will heat the dialysate to about 37° C. or above. Heating plates 496 to about 70° C. will increase the outlet dialysate temperature to about 55° C.

FIG. 7 illustrates that heating plates 496a to 496d to a temperature of about 47° C. requires about 430 to about 440 Watts of power. Heating the plates to a temperature of about 70° C. requires about 880 to about 890 Watts of power.

FIG. 8 relates heater plate temperature to dialysate pressure drop occurring along heating pathway 498. As plate temperature increases, the corresponding pressure drop decreases. Heating plates 496a to 496d to a temperature of about 47° C. causes a corresponding pressure drop of about 0.15 psig. This pressure drop is manageable given the operating pressure of the medical fluid pump of system 10, which can be about two to three psig.

As mentioned above, heater 480 can be modified to have more or fewer plates 496 which are heated to lower or higher temperatures, respectively. Plates 496 can be varied to have different aspect ratios (length l to depth d ratio). Plates 496 may be smooth or textured. Heater 480 can also be configured such that plates 496 contact the fluid or dialysate directly or are alternatively provided with a film, such as a plastic film. Further alternatively, secondary coil plates 496 may be incorporated into unit 60 of system 10, reducing the cost of the disposable cassette 50. Here, pathway 498 can serpentine back and forth within a disposable pathway, which is positioned along one or more plates 496 located within unit 60. For example, unit 60 can have a clamshell shape, wherein plates 496 are disposed on opposing inner surfaces of the clamshell. The disposable pathway is placed between and in contact with the disposable pathway. Here, plates 496 can be of a material optimized for heat transfer since the plates do not contact the fluid directly.

Figure 9:
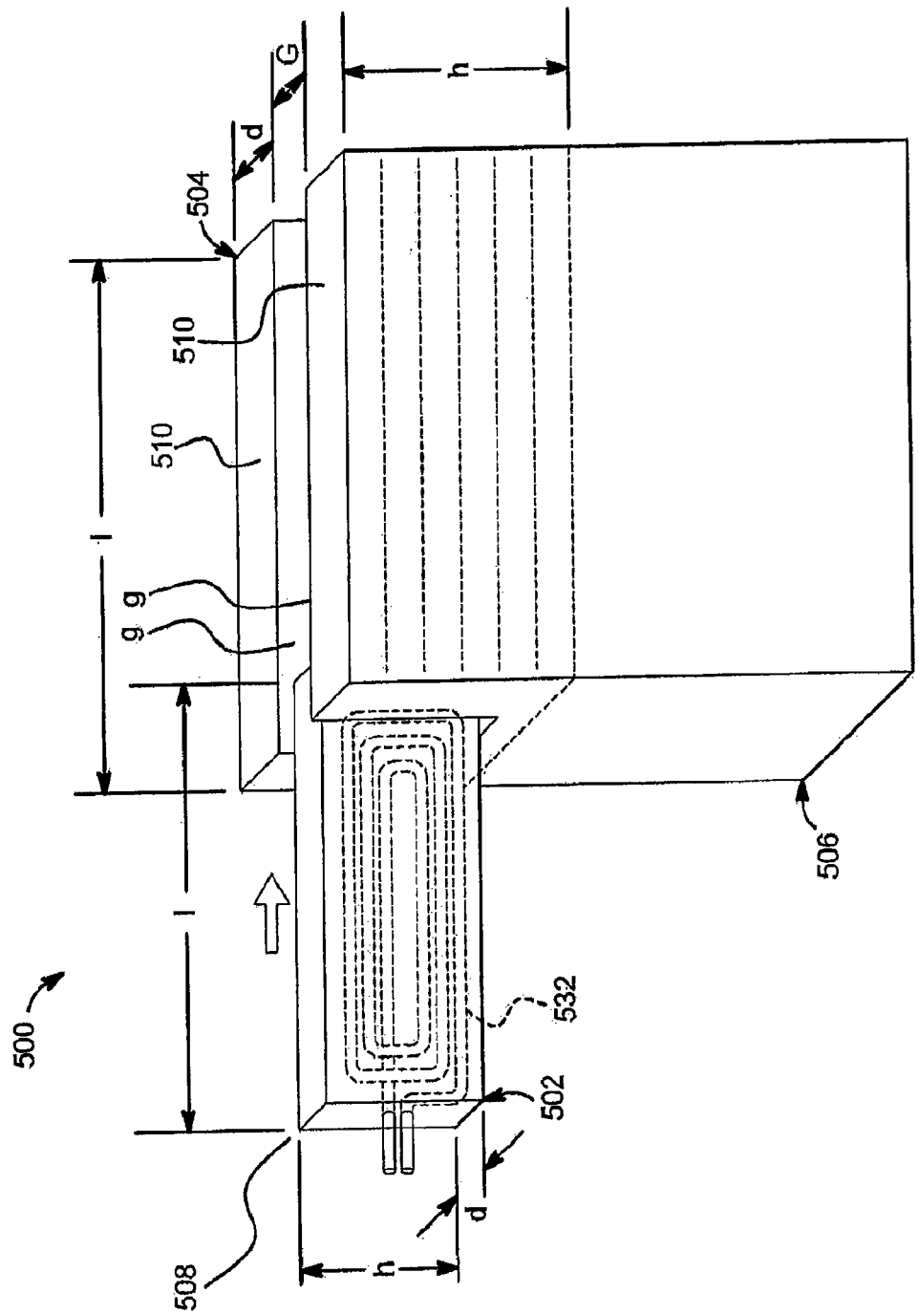
FIG. 9 is a perspective view of a second embodiment of an inductive disposable-cassette mountable dialysis fluid heater.
Figure 10:
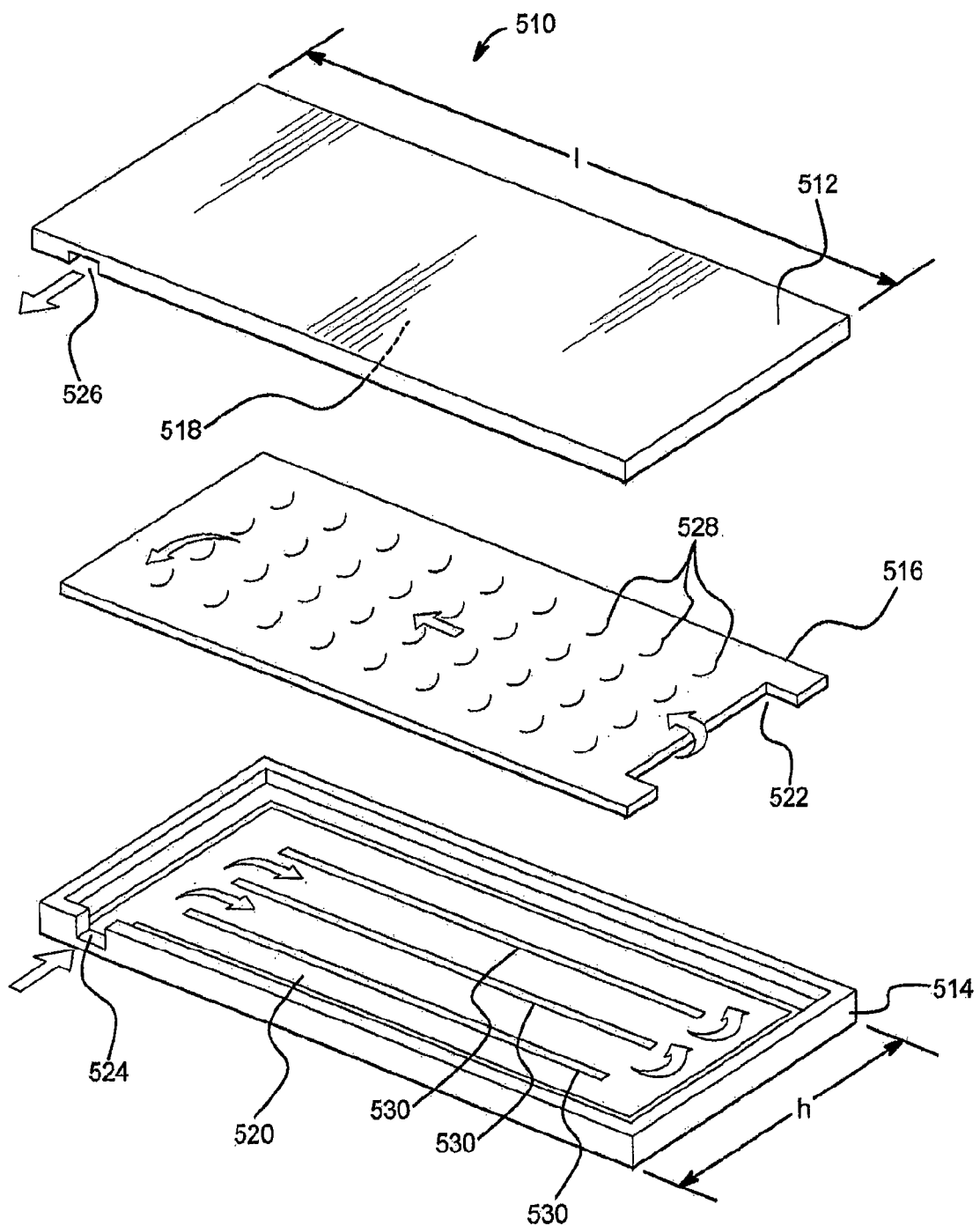
FIG. 10 is a perspective view of the heater of FIG. 9 incorporated into a disposable-cassette.

Referring now to FIGS. 9 and 10, an alternative embodiment of an inductive, inline fluid heater is illustrated by heater 500. The primary components of heater 500 include an induction coil block 502, which fits inside of or adjacent to a disposable fluid heat channel 504. In the illustrated embodiment, fluid heating channel 504 is U-shaped and fits around the sides of induction coil block 502. Alternatively, heating channel 504 is exposed to only a single surface of induction coil block 502.

Induction coil block 502 in one embodiment is provided as part of the hardware unit 60 of system 10. Fluid heating channel 504 in one embodiment is formed integrally with (and is, e.g., upstream of) cassette area 506 of the disposable cassette, which is dedicated to pumping and valving. Locating fluid heating channel 504 of the cassette upstream of the pumping and valving portion 506 of the disposable cassette helps to reduce the amount of temperature compensation needed for pumping accuracy.

As discussed above with heater 480, the inline nature of heaters 480 and 500 eliminates the need for a batch warmer bag. The relatively rigid inductive heating systems 480 and 500 can be less "floppy" than batch heating systems and thereby easier to load. System 500 is constructed so that fluid heating channel 504 is readily aligned and made operable with induction coil block 502.

One set of suitable dimensions for heater 500 is set forth below. The dimensions serve as an illustrative example and in no way are meant to limit the scope of the disclosure. Block 502 includes an e.g., plastic housing 508, which in an embodiment is shaped as a flat plate having overall dimensions l×h×d of about 2 inches×2 inches×0.125 inch thick (5.08 cm×5.08 cm×3.18 mm) or 1 inch×4 inches×0.125 inch thick (2.54 cm×10.2 cm×3.18 mm). Housing 508 holds coil 532. Coil 532 can be any suitable metal because it does not contact the dialysate directly, such as, steel or stainless steel. Coil 532 in one preferred embodiment is Litz Wire. Coil 532 in one embodiment is a three inch diameter pancake type coil.

Fluid heating channel 504 includes a pair of sub-channels 510, which form the sides of the U-shaped channel 504. Each sub-channel 510 of U-shaped channel 504 in one embodiment has overall dimensions l×h×d of about 2.5 inches×2.5 inches×0.25 inch thick (6.35 cm×6.35 cm×6.35 mm) or about 1.5 inches×4.5 inches×0.25 inch thick (3.81 cm×11.4 cm×6.35 mm). The sub-channels 510 define a gap G between the sub-channels. In one implementation, the clearance or little gap g between each of the outer surfaces of induction coil block 502 and the opposing inner surfaces of sub-channels 510 of fluid heating channel 504 is just enough to allow induction coil block 502 to fit within gap G.

Referring now to FIG. 10, one of the sub-channels 510 is shown exploded. Each sub-channel 510 includes a first cover portion 512 and a second cover portion 514, which surrounds a heater plate 516. Heater plate 516 is sized to create first and second fluid flow plenums 518 and 520, between the top surface of plate 516 and the bottom surface of first cover portion 512 and the bottom surface of plate 516 and the top surface second cover portion 514, respectively. Covers 512 and 514 are plastic in one embodiment and are sealed together via any of the methods described herein. Plenums 518 and 520 can each have a volume defined by the dimensions for sub-channels 510 set forth above.

Plate 516 is sized to fit within the walls of covers 512 and 514. Plate 516 defines a notch 522 that allows fluid or dialysate to flow from second plenum 520 to first plenum 518, respectively, as indicated by the arrows shown in FIG. 10. Lower cover portion defines a fluid inlet 524, which receives fluid from: (i) a supply bag 14, 16 or 22; (ii) cassette portion 506; or (iii) the other sub-channel 510 depending upon whether the illustrated sub-channel 510 is upstream or downstream of the other sub-channel 510. Likewise, upper cover portion 512 defines an outlet 526, through which dialysate exits sub-channel 510 to: (i) cassette portion 506; (ii) the patient; or (iii) the other non-illustrated sub-channel 510.

Heating plate 516 can be any suitable medically compatible and inductively heatable material such as stainless steel. As illustrated, plate 516 can have perforations, ribs, baffles or other flow obstructions 528, which: (i) increase surface area contact with the dialysate; (ii) increase contact time; (iii) turbulate the fluid flow; and (iv) increase the efficiency of heater 500. First and second cover portions 512 and 514 can additionally or alternatively have internal ribs or baffling, such as ribs 530, which direct and/or turbulate the flow of dialysate through plenums 518 and 520, respectively.

Figure 11:
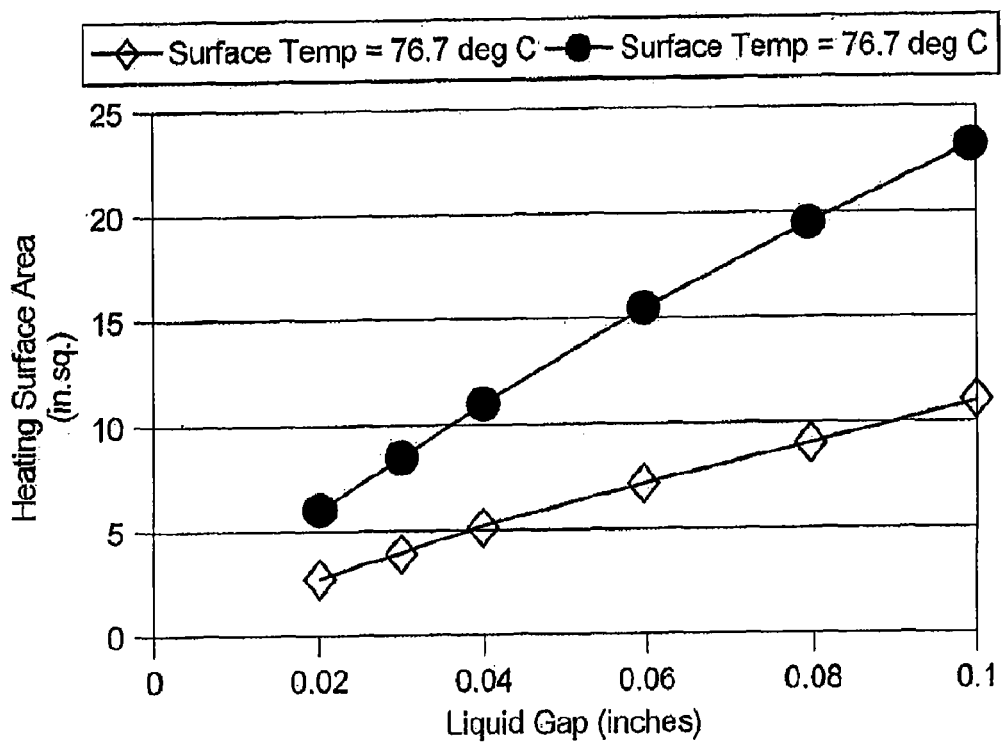
FIG. 11 is a chart relating heating surface area and liquid gap given a specified heating requirement for the heater of FIG. 9.

Referring now to FIG. 11, a chart is shown that relates the combined surface area of plates 516 of both sub-channels 510 required to heat dialysate from 5° C. to 37° C. at a flowrate of 200 mL/min as a function of gap for two different plate temperatures. The gap here is the distance between plate 516 and the inner surfaces of covers 512 and 514. As illustrated, the required combined surface area for a plate temperature of 76.7° C. (diamonds) ranges from about 2.5 in$^2$ (6.4 cm$^2$) to about 11 in$^2$ (30 cm$^2$) as the gap increases from about 0.03 inch (0.76 mm) to about 0.1 inch (2.5 mm). The required total surface area (circles) for a plate temperature of 47° C. ranges from about 6 in$^2$ (15.2 cm$^2$) to about 23.5 in$^2$ (59.7 cm$^2$) for the same gap range. The gap size is chosen to balance heating efficiency with providing enough space so that flow through heater 500 does not become obstructed. As with heater 480, suitable filtration may be placed upstream of heater 500 to remove at least most of the particles that could block the flow path(s) within heater 500.

Figure 12:
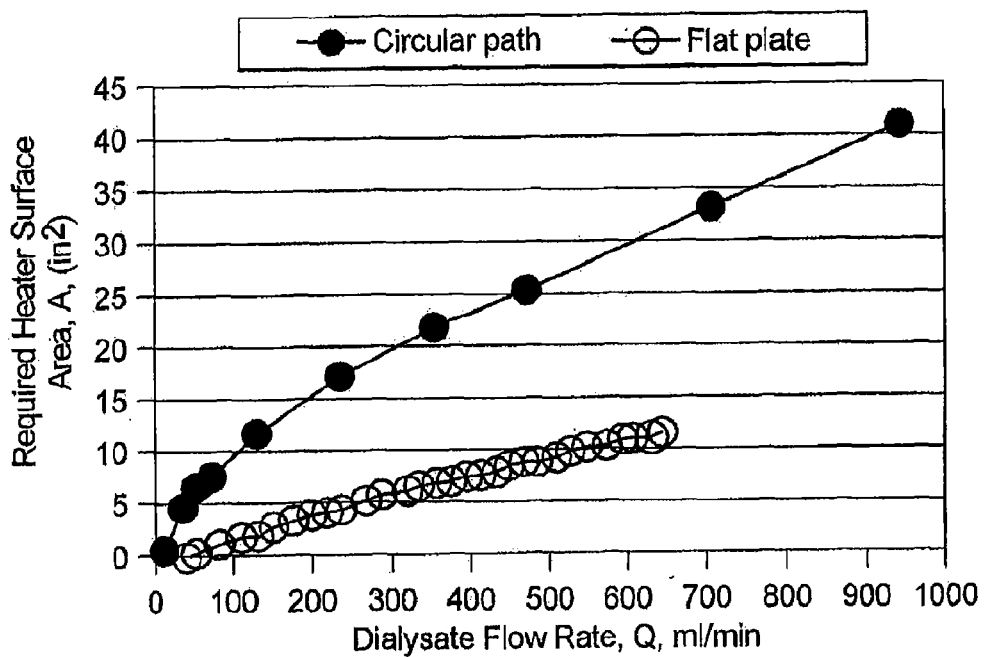
FIG. 12 is a chart relating heating surface area and dialysate flowrate for circular path versus flat plate inductive heaters.

FIG. 12 is a chart relating required heating surface area for the temperature rise described above for the chart of FIG. 11. A gap of 0.04 inches (1.0 mm) and a surface temperature of 170° F. (77° C.) for two different inductive heaters, namely, a circular flow path (dark circles) heater and a flat plate heater (light circles), such as heater 500. One example of an inductive fluid heater having a circular flow path is described in commonly owned patent application Ser. No. 10/982,170, entitled "High Convection Home Hemodialysis/Hemofiltration and Sorbent System," filed Nov. 5, 2004, the entire contents of which are incorporated herein by reference.

Summarizing the disclosure of the referenced application briefly, the heater in that application is cylindrically shaped with inner and outer tubes cooperating with a cylindrical element to form the dialysate flow path. Cold fluid is pumped into the induction heater along the inside of the outer tube and the outside of the heater element, around the bottom of the element, then along the inside of the element and outside of the inner tube before finally exiting the heater from the top.

For the cylindrical inductive heater, initial calculations have been made, which indicate that a surface area of less than ten square inches is required to heat the fluid from 5° C. to 37° C. degrees at a dialysate flowrate of approximately 150 ml/min. Using both sides of the element, ten square inches equates to a heater element sized for example at approximately one inch (2.54 cm) in diameter by about 1.5 inches (3.81 cm) long. This results advantageously in a small fluid heater.

As seen in FIG. 12, the required surface area for a circular flow path heater varies non-linearly to about 41 in$^2$ (104 cm$^2$) as flowrate increases to over 900 mL/min. The required surface area for the flat plate flow path varies more linearly to about 12 in$^2$ (30.5 cm$^2$) as flowrate increases to over 600 mL/min. Flat plate heater 500 appears to be more efficient than the circular flow path heater incorporated above by reference.

Figure 13:
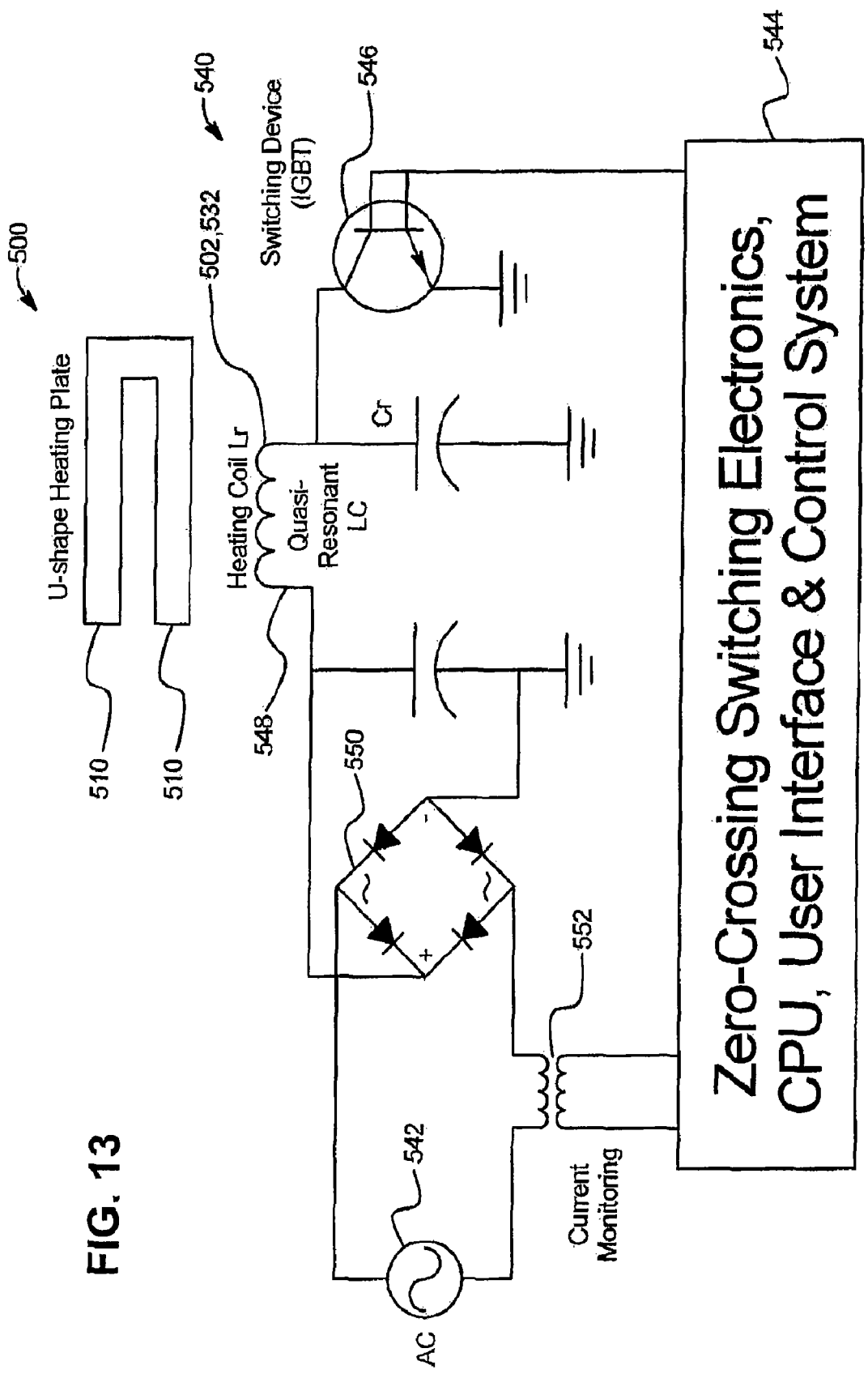
FIG. 13 is an electrical schematic for the inductive heaters of FIGS. 4/5 and 9/10.

Referring now to FIG. 13, an electrical system 540 for both heaters 480 and 500 is illustrated. Electrical system 540 includes an alternating current voltage source 542, which can be for example a 120 VAC or 240 VAC house or facility supply voltage. System 540 includes a control system 544, which can include a supervisory control processor, a delegate control processor or both. System 544 can also include one or more safety processor that monitors the operation of heater 480 or 500 to ensure its proper operation. At least one of the processors operates with a user interface, such as a display panel. The processor can control power to the primary coil based on feedback concerning any one or more of: (i) the temperature of the secondary coil, (ii) the temperature of the heated fluid, (iii) the initial temperature of the fluid, and (iv) the flowrate of the fluid. The feedback is provided by suitably placed temperature/flow sensors. The user interface allows the user to set dialysate temperature and dialysate flowrate for example. Control system 544 also houses zero-crossing switching electronics in one embodiment, which is well suited for high efficiency transistor switching.

The zero-crossing switching electronics operate an insulated gate bipolar transistor ("IGBT") type switching device 546. The IGBT device 546 in one embodiment is an IGBT 60 amp, 1 kV device, which has zero voltage across the associated transistor and zero current through the transistor. IGBT switching device 546 in turn controls a quasi-resonant LC circuit 548, which energizes the primary coil 532 of unit 502. A quasi-resonant LC circuit 548 is used in one embodiment. Coil 532 of unit 502 in can range from about 80 to about 170 uH in inductance. Coil 532 can be energized to ten amperes (wire capability) and have a pancake coil diameter of about three inches (7.6 cm). Circuit 548 can have a resonant frequency of about 30 KH to 50 KH. The power requirement from source 542 is for example from about 300 W to about 600 W. A bridge rectifier 550 is connected between power source 542 and quasi-resonant LC circuit 548.

It should be understood that various changes and modifications to the presently preferred embodiments described herein will be apparent to those skilled in the art. Such changes and modifications can be made without departing from the spirit and scope of the present disclosure and without diminishing its intended advantages. It is therefore intended that such changes and modifications be covered by the appended claims.

The disclosure is claimed as follows:
1. A medical fluid machine comprising:
an enclosure;
a disposable unit accepted by the enclosure, the disposable unit including a conduit through which a medical fluid can flow, the conduit including a first tubular end, a second tubular end, and a flattened viewing portion, wherein the first and second tubular ends transition to the flattened viewing portion;
a light source configured and arranged to emit light onto the viewing portion of the conduit;
a camera focused on the viewing portion of the conduit; and
a processor operable with the camera configured to determine a speed of a particle entrained in the medical fluid based on at least two images of the particle in the viewing portion taken by the camera.

2. The medical fluid machine of claim 1, wherein the disposable unit includes at least one characteristic selected from the group consisting of: (i) having an at least semi-rigid valve portion; (ii) having a flexible pumping portion; (iii) having a tube configured to operate with a peristaltic pump; (iv) having a flow path portion for the medical fluid to be heated; (v) having an air trap portion; (vi) the conduit being a rigid pathway formed in the disposable unit; and (vii) the conduit being a tube connected fluidly to the disposable unit.

3. The medical fluid machine of claim 1, wherein the light source includes at least one characteristic selected from the group consisting of: (i) employing a light emitting diode ("LED") or laser diode; (ii) including multiple lights configured to illuminate the viewing portion from multiple angles; (iii) being positioned on a side of the viewing position that is at least substantially opposite from a side of the viewing portion that the camera is positioned; (iv) being positioned on a side of the viewing portion that is at least substantially the same as the side of the viewing portion that the camera is positioned; (v) being positioned on a side of the viewing portion that is at an angle with respect to a side of the viewing portion that the camera is positioned; (vi) being illuminated intermittently and in sync with when the camera is taking images of the viewing portion; and (vii) being a high intensity light source.

4. The medical fluid machine of claim 1, wherein the light source is configured to be at least one of: (i) lighted sequentially when the light source includes multiple light emitting elements and (ii) positioned so that light reflecting off the viewing portion does not impinge the camera.

5. The medical fluid machine of claim 1, wherein the camera includes at least one characteristic selected from the group consisting of: (i) having a frame rate of at least five hundred frames per second; (ii) being monochrome; and (iii) being capable of color imaging.

6. The medical fluid machine of claim 1, wherein the viewing portion includes at least one characteristic selected from the group consisting of: (i) being formed in the conduit; (ii) being spliced into the conduit; (iii) being connected to the conduit; (iv) having a relatively high aspect ratio; (v) being at least substantially rectangular; (vi) being relatively thin; (vii) being configured so that the particle tends not to be masked by another particle; and (viii) having a known cross-sectional area.

7. The medical fluid machine of claim 1, wherein the processor includes at least one characteristic selected from the group consisting of: (i) being configured to determine at least one of a quantity, size, type and velocity of the particle in the medical fluid; (ii) being configured to determine at least one of the speed, velocity and the volumetric fluid flowrate of the medical fluid; (iii) being a digital signal processor; and (iv) being operable with an assumption that the particles are distributed across the entire cross-section of the viewing portion.

8. The medical fluid machine of claim 1, which includes an apparatus configured and arranged to induce vibrations into the medical fluid flowing through the viewing portion.

9. A medical fluid flowrate detector comprising:
- a light source configured and arranged to emit light onto a flattened viewing portion of a conduit carrying a medical fluid;
- the conduit including a first tubular end and a second tubular end, wherein the first and second tubular ends transition to the flattened viewing portion;
- a camera focused on the viewing portion of the conduit; and
- a processor operable with the camera and configured to: (i) determine a speed of a particle entrained in the medical fluid based on at least two images of the particle in the viewing area taken by the camera; and (ii) determine a flowrate of the medical fluid based on the speed of the particle and a geometry of the viewing portion.

10. The medical fluid flowrate detector of claim 9, wherein the processor includes at least one characteristic selected from the group consisting of: (i) being configured to determine at least one of a quantity, size, type and velocity of the particle in the medical fluid; (ii) being configured to determine at least one of the speed, velocity and the volumetric fluid flowrate of the medical fluid; (iii) being a digital signal processor; and (iv) being operable with an assumption that the particles are distributed across the entire cross-section of the viewing portion.

11. The medical fluid flowrate detector of claim 9, wherein the light source includes at least one characteristic selected from the group consisting of: wherein the light source includes at least one characteristic selected from the group consisting of: (i) employing a light emitting diode ("LED") or laser diode; (ii) including multiple lights configured to illuminate the viewing portion from multiple angles; (iii) being positioned on a side of the viewing position that is at least substantially opposite from a side of the viewing portion that the camera is positioned; (iv) being positioned on a side of the viewing portion that is at least substantially the same as the side of the viewing portion that the camera is positioned; (v) being positioned on a side of the viewing portion that is at an angle with respect to a side of the viewing portion that the camera is positioned; (vi) being illuminated intermittently and in sync with when the camera is taking images of the viewing portion; and (vii) being a high intensity light source.

12. The medical fluid flowrate detector of claim 9, wherein the light source is configured to be at least one of: (i) lighted sequentially when the light source includes multiple lights and (ii) positioned so that light reflecting off the viewing portion does not impinge the camera.

13. The medical fluid flowrate detector of claim 9, wherein the camera includes at least one characteristic selected from the group consisting of: (i) having a frame rate of at least five hundred frames per second; (ii) being monochrome; and (iii) being capable of color imaging.

14. The medical fluid flowrate detector of claim 9, wherein the viewing portion includes at least one characteristic selected from the group consisting of: (i) being formed in the conduit; (ii) being spliced into the conduit; (iii) being connected to the conduit; (iv) having a relatively high aspect ratio; (v) being at least substantially rectangular; (vi) being relatively thin; (vii) being configured so that the particle tends not to be masked by another particle; and (viii) having a known cross-sectional area.

15. The medical fluid flowrate detector of claim 9, which is configured to operate with at least one medical fluid device selected from the group consisting of: a dialysis machine and a drug infusion machine.

16. A medical fluid machine comprising: a fluid carrying unit including a conduit through which a medical fluid can flow, the conduit including a first tubular end, and a second tubular end wherein the first and second tubular ends transition to the flattened viewing portion; a light source configured and arranged to emit light onto the viewing portion of the conduit; a camera focused on the viewing portion of the conduit; and a processor operable with the camera and configured to determine that a particle entrained in the medical fluid is an air bubble based on determined shape of the bubble.

17. The medical fluid machine of claim 16, wherein the fluid carrying unit is disposable.

18. The medical fluid machine of claim 16, wherein the determined shape for an air bubble is an at least substantially circular or rectangular shape.

19. The medical fluid machine of claim 16, wherein the process is configured to determine that the particle is an air bubble when a reflected highlight indicative of a spherical shape is detected by the camera.

20. The medical fluid machine of claim 16, wherein the processor is configured to determine that a particle entrained in the medical fluid is an acceptable therapy particle when a determined shape of the particle is irregular.

* * * * *